United States Patent
Mougeot et al.

(10) Patent No.: US 10,954,571 B2
(45) Date of Patent: Mar. 23, 2021

(54) COMPOSITIONS AND METHODS FOR ORAL MICROBIOME SIGNATURES

(71) Applicant: The Charlotte Mecklenburg Hospital Authority, Charlotte, NC (US)

(72) Inventors: Farah K. B. Mougeot, Charlotte, NC (US); Jean-Luc C. Mougeot, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 400 days.

(21) Appl. No.: 15/632,091

(22) Filed: Jun. 23, 2017

(65) Prior Publication Data

US 2018/0010171 A1    Jan. 11, 2018

Related U.S. Application Data

(60) Provisional application No. 62/354,029, filed on Jun. 23, 2016.

(51) Int. Cl.
| | |
|---|---|
| C12Q 1/689 | (2018.01) |
| C12Q 1/6886 | (2018.01) |
| G01N 33/574 | (2006.01) |
| G01N 33/569 | (2006.01) |

(52) U.S. Cl.
CPC .......... *C12Q 1/689* (2013.01); *C12Q 1/6886* (2013.01); *G01N 33/56911* (2013.01); *G01N 33/574* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

PUBLICATIONS

Keene et al., Oral Surgery, Oral Medicine, Oral Pathology, vol. 78, No. 5, pp. 577-582 (1994).*
Epstein et al., Oral Surgery, Oral Medicine, Oral Pathology, vol. 86, No. 3, pp. 286-292 (1998).*
Keene et al., Oral Surgery, Oral Medicine, Oral Pathology, vol. 78, No. 5, pp. 577-582 (1994) (of record). (Year: 1994).*
Epstein et al., Oral Surgery, Oral Medicine, Oral Pathology, vol. 86, No. 3, pp. 286-292 (1998) (of record). (Year: 1998).*
Bowden, G. H. "Does assessment of microbial composition of plaque/saliva allow for diagnosis of disease activity of individuals?" *Community Dentistry and Oral Epidemiology* 25:76-81 (1997) (Abstract Only).
"Dental Team, Oral Complications of Cancer Treatment: What the Dental Team Can Do" *U.S. Department of Health and Human Services, National Institutes of Health* www.nidcr.nih.gov Publication No. 09-4372 (8 pages) (2009).
Dewhirst, Floyd E. "The Oral Microbiome: Critical for Understanding Oral Health and Disease" *Journal California Dental Association* 44(7):409-410 (2016).
Gade et al. "Graph based fusion of miRNA and mRNA expression data improves clinical outcome prediction in prostate cancer" *BMC Bioinformatics* 12(488):1-10 (2011).
"Homings: Human Oral Microbe Identification using Next Generation Sequencing" *The Forsyth Institute* http://homings.forsyth.org/index2.html (3 pages) (2016).
Jellema et al. "Impact of radiation-induced xerostomia on quality of life after primary radiotherapy among patients with head and neck cancer" *International Journal of Radiation Oncology Biology Physics* 69(3):751-760 (2007) (Abstract Only).
Kaidonis et al. "The 'sialo-microbial-dental complex' in oral health and disease" *Annals of Anatomy* 203:85-89 (2016).
Kanasi et al. "Microbial Risk Markers for Childhood Caries in Pediatricians' Offices" *Journal of Dental Research* 89:378-383 (2010).
Keefe et al. "Updated Clinical Practice Guidelines for the Prevention and Treatment of Mucositis" *Cancer* 109:820-831 (2007).
Mougeot et al. "Concordance of HOMIM and HOMINGS technologies in the microbiome analysis of clinical samples" *Journal of Oral Microbiology* 8:1-9 (2016).
Mougeot et al. "Oral Microbiome in Head and Neck Cancer: A Longitudinal Study" *94th General Session & Exhibition of the IADR* (1 page) (2016).
Mougeot et al. "Oral Microbiome Shifts in Head and Neck Cancer" *94th General Session & Exhibition of the IADR* (1 page) (2016).
PDQ Cancer Information Summaries "Oral Complications of Chemotherapy and Head/Neck Radiation (PDQ®)" *National Cancer Institute* (US) (69 pages) (2016).
Schmidt et al. "Changes in Abundance of Oral Microbiota Associated with Oral Cancer" *PLoS ONE* 9(6):e98741 (2014).
Segata et al. "Composition of the adult digestive tract bacterial microbiome based on seven mouth surfaces, tonsils, throat and stool samples" *Genome Biology* 13:R42 (2012).
Shiboski et al. "Management of salivary hypofunction during and after radiotherapy" *Oral Surgery, Oral Medicine, Oral Pathology, Oral Radiology, and Endodontology* 103(Supplement):S66.e1-S66.e19 (2007) (Abstract Only).
Sonis et al. "Perspectives on Cancer Therapy-Induced Mucosal Injury: Pathogenesis, Measurement, Epidemiology, and Consequences for Patients" *Cancer* 100:1995-2025 (2004).
Tanner et al. "Understanding Caries From the Oral Microbiome Perspective" *Journal of the California Dental Association* 44(7):437-446 (2016).
Wade "The oral microbiome in health and disease" *Pharmacological Research* 69(1):137-143 (2013) (Abstract Only).

* cited by examiner

*Primary Examiner* — Soren Harward
*Assistant Examiner* — Paul D. Pyla
(74) *Attorney, Agent, or Firm* — Myers Bigel, P.A.

(57) ABSTRACT

The present invention provides methods and compositions involving microbiome signatures and their association with oral complications of cancer therapy.

4 Claims, 10 Drawing Sheets

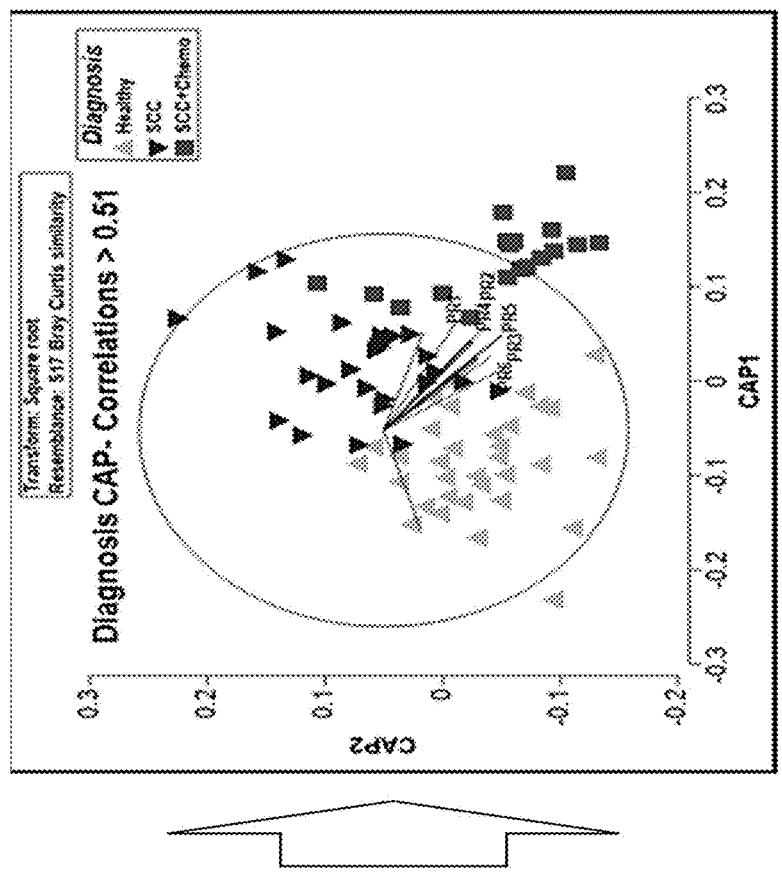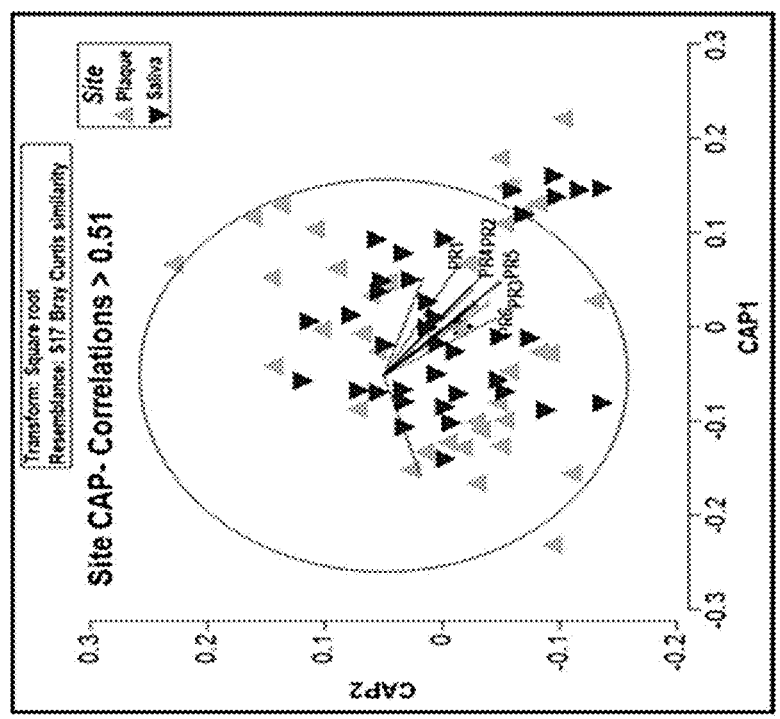
Figure 2

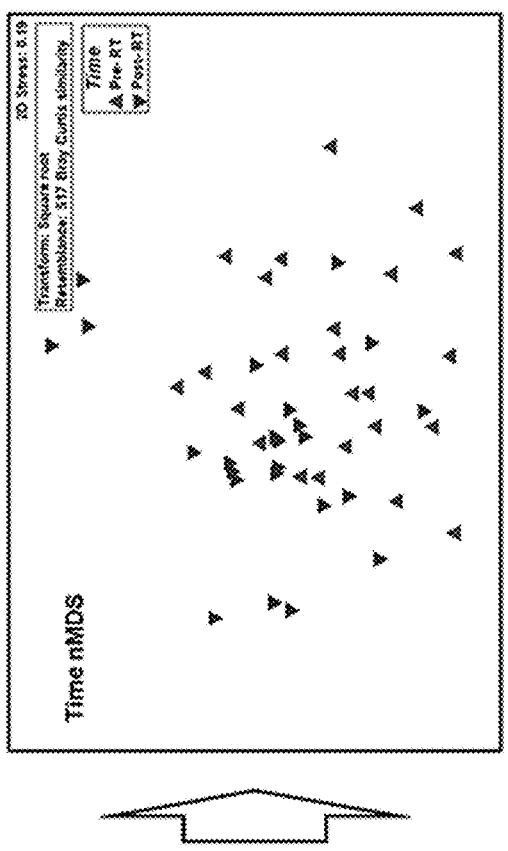
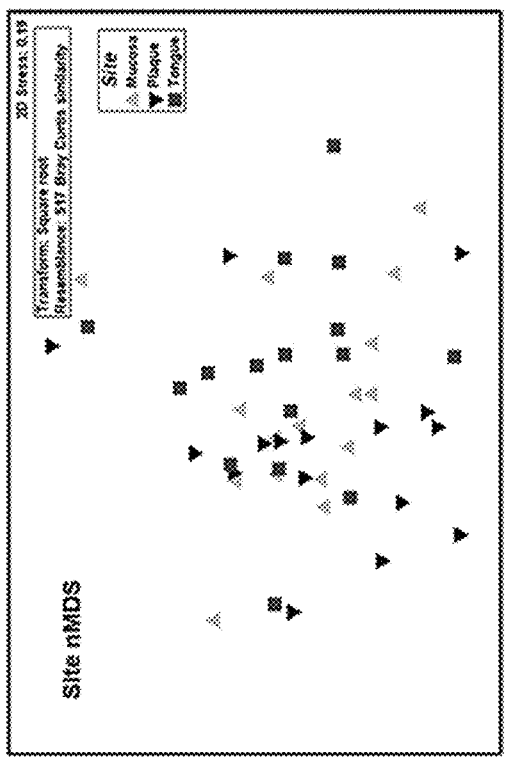
Figure 3

Figure 8

```
PERMANOVA
Permutational MANOVA
```
*Resemblance worksheet*
```
Name: Resem1
Data type: Similarity
Selection: All
Transform: Square root
Resemblance: S17 Bray Curtis similarity
Sums of squares type: Type III (partial)
Fixed effects sum to zero for mixed terms
Permutation method: Permutation of residuals under a reduced model
Number of permutations: 9999
```
*Factors*

| Name | Abbrev. | Type | Levels |
|---|---|---|---|
| Site | Si | Fixed | 3 |
| Group | Gr | Random | 3 |
| Time | Ti | Fixed | 2 |
| SUBJECT | SU | Random | 8 |

*Contrasts*

| Name | Abbrev. | Factor | Contrast |
|---|---|---|---|
| C1 | C1 | Site | (Mucosa)v(Plaque) |
| C2 | C2 | Site | (Mucosa)v(Tongue) |
| C3 | C3 | Site | (Plaque)v(Tongue) |
| C1 | C1 | Group | (Control)v(Chemo) |
| C2 | C2 | Group | (Control)v(AntiBio) |
| C3 | C3 | Group | (Chemo)v(AntiBio) |

*Excluded terms:* TimexSUBJECT (Group)(Site))
*PERMANOVA table of results*

| Source | df | SS | Unique MS | Pseudo-F | P(perm) | perms | P(MC) | |
|---|---|---|---|---|---|---|---|---|
| Si | 2 | 7298.2 | 3649.1 | 1.411 | 0.1397 | 9913 | 0.1358 | |
| C1 | 1 | 2280 | 2280 | 0.80491 | 0.63 | 9929 | 0.6203 | |
| C2 | 1 | 3484.9 | 3484.9 | 1.543 | 0.1782 | 9947 | 0.164 | |
| C3 | 1 | 5182.4 | 5182.4 | 1.9428 | 0.056 | 9915 | 0.0667 | Time |
| Ti | 1 | 6942.6 | 6942.6 | 3.7887 | 0.0223 | 9957 | 0.003 | P-value |
| Gr(Si) | 6 | 15501 | 2583.4 | 0.9504 | 0.5801 | 9821 | 0.5815 | |
| Gr(C1) | 4 | 11329 | 2832.2 | 0.9941 | 0.479 | 9873 | 0.4974 | |
| Gr(C2) | 4 | 9006.8 | 2251.7 | 0.87083 | 0.6831 | 9881 | 0.6786 | |
| Gr(C3) | 4 | 10666 | 2666.4 | 0.98028 | 0.5177 | 9844 | 0.503 | |
| C1(Si) | 3 | 7311.2 | 2437.1 | 1.0117 | 0.4442 | 9911 | 0.4556 | |
| C2(Si) | 3 | 9305.4 | 3101.8 | 1.1075 | 0.3289 | 9907 | 0.3284 | |
| C3(Si) | 3 | 6323.2 | 2107.7 | 0.72241 | 0.8327 | 9908 | 0.8216 | |
| SixTi | 2 | 2311.8 | 1155.9 | 0.63079 | 0.7784 | 9938 | 0.8765 | Site x Time |
| C1xTi | 1 | 918.44 | 918.44 | 0.56623 | 0.7054 | 9729 | 0.8058 | Interaction |
| C2xTi | 1 | 982.46 | 982.46 | 0.50161 | 0.7161 | 9726 | 0.8569 | P-value |
| C3xTi | 1 | 1566.8 | 1566.8 | 0.81743 | 0.527 | 9731 | 0.5995 | |
| Su (Gr(Si)) | 15 | 40774 | 2718.2 | 1.5309 | 0.0011 | 9797 | 0.0037 | |
| SU(Gr(C1)) | 10 | 28490 | 2849 | 1.6501 | 0.0011 | 9823 | 0.0086 | |
| SU(Gr(C2)) | 10 | 25857 | 2585.7 | 1.4588 | 0.0187 | 9839 | 0.0419 | |
| SU(Gr(C3)) | 10 | 27200 | 2720 | 1.4882 | 0.0057 | 9840 | 0.0218 | |
| SU(C1(Si)) | 9 | 21680 | 2408.9 | 1.2086 | 0.1941 | 9868 | 0.2265 | |
| SU(C2(Si)) | 12 | 33609 | 2800.7 | 1.4708 | 0.0096 | 9827 | 0.0192 | |
| SU(C3(Si)) | 9 | 26259 | 2917.7 | 2.1044 | 0.0004 | 9854 | 0.0017 | |
| Gr(Si)xTi | 6 | 11002 | 1833.7 | 1.0327 | 0.4269 | 9852 | 0.4205 | Group(Site) |
| Gr(C1)xTi | 4 | 6479.3 | 1619.8 | 0.9382 | 0.5763 | 9899 | 0.5688 | x Time |
| Gr(C2)xTi | 4 | 7850 | 1962.5 | 1.1072 | 0.3336 | 9895 | 0.3487 | Interaction |
| Gr(C3)xTi | 4 | 7674.6 | 1918.5 | 1.0498 | 0.4015 | 9882 | 0.4051 | P-value |
| C1(Si)xTi | 3 | 6417.7 | 2139.2 | 1.0733 | 0.396 | 9921 | 0.4006 | |
| C2(Si)xTi | 3 | 6764.3 | 2254.8 | 1.1841 | 0.253 | 9893 | 0.2836 | |
| C3(Si)xTi | 3 | 3068.3 | 1022.8 | 0.7377 | 0.8353 | 9888 | 0.7887 | |
| Res | 15 | 26633 | 1775.6 | | | | | |
| Total | 47 | 11118E5 | | | | | | |

Figure 9

| PERMANOVA- Ex. Chemo and Antibiotic Groups |
| --- |
| Permutational MANOVA |
| *Resemblance worksheet* |
| Name: Resem1 |
| Data type: Similarity |
| Selection: All |
| Transform: Square root |
| Resemblance: S17 Bray Curtis similarity |
| Sums of squares type: Type III (partial) |
| Fixed effects sum to zero for mixed terms |
| Permutation method: Permutation of residuals under a reduced model |
| Number of permutations: 9999 |

*Factors*

| Name | Abbrev. | Type | Levels |
| --- | --- | --- | --- |
| Site | Si | Fixed | 3 |
| Time | Ti | Fixed | 2 |
| SUBJECT | SU | Random | 3 |

*Excluded terms*
Time x SUBJECT (Site)

*PERMANOVA table of results*

| Source | df | SS | MS | Pseudo-F | P(perm) | Unique perms | P(MC) | |
| --- | --- | --- | --- | --- | --- | --- | --- | --- |
| Si | 2 | 3256.5 | 1628.3 | 0.67307 | 0.8091 | 280 | 0.7718 | Time p-value |
| Ti | 1 | 9370.4 | 9370.4 | 3.9718 | 0.0157 | 9950 | 0.0184 | |
| SU(Si) | 6 | 14515 | 2419.1 | 1.0254 | 0.4654 | 9913 | 0.4676 | |
| SixTi | 2 | 2789.4 | 1394.7 | 0.59116 | 0.8028 | 9947 | 0.7807 | Site intersection p-value |
| Res | 6 | 14155 | 2359.2 | | | | | |
| Total | 17 | 44087 | | | | | | |

Figure 10

| SIMPER Analysis | | | | | | | |
|---|---|---|---|---|---|---|---|
| *Groups Cancer & Radiation* <br> Average dissimilarity = 69.56 | | | | | | | |
| Group Cancer | | Group Radiation | | | | | Abund |
| Species | Av. Abund | Av. Abund | Av. Diss | Diss/SD | Contrib% | Cum.% | Ratio |
| AL | 3.90 | 2.62 | 0.29 | 0.94 | 0.41 | 66.78 | |
| PR1 | 2.71 | 4.41 | 0.28 | 1.01 | 0.41 | 67.19 | 1.63 |
| PR | 1.63 | 3.78 | 0.28 | 0.39 | 0.41 | 67.59 | |
| SE | 1.93 | 1.51 | 0.15 | 0.90 | 0.21 | 82.59 | |
| PR2 | 0.80 | 2.12 | 0.14 | 0.76 | 0.21 | 82.80 | 2.65 |
| CA | 2.12 | 0.98 | 0.14 | 0.63 | 0.20 | 83.00 | |

COMPOSITIONS AND METHODS FOR ORAL MICROBIOME SIGNATURES

STATEMENT OF PRIORITY

This application claims the benefit, under 35 U.S.C. § 119(e), of U.S. Provisional Application Ser. No. 62/354,029, filed Jun. 23, 2016, the entire contents of which are incorporated by reference herein.

FIELD OF THE INVENTION

The present invention relates to oral microbiome signatures and their association with oral complications in patients receiving radiation and/or chemotherapy for head and neck cancers.

BACKGROUND OF THE INVENTION

Conventional dental/oral cavity examination methods cannot predict oral complications or outcomes due to cancer therapy and not based on methods following the changes in oral microbiome composition and gene expression that in essence alter oral health. Therefore, personalized preventative and/or curative treatment cannot be implemented for a clinically heterogeneous cancer patient population. Head and neck cancer patients may present to the dental clinic with variable past history of radiation therapy, chemotherapy and/or antibiotic treatments, different cancer stages, and primary sites of oral cancer development, and are possibly scheduled for further radiation and/or chemotherapy treatments.

The present invention overcomes previous shortcomings in the art by providing methods and compositions employing oral microbiome signatures as biomarkers for prediction of risk, progression and response to treatment for oral complications associated with cancer therapy.

BRIEF DESCRIPTION OF THE DRAWINGS

FIG. 2. Post-PERMANOVA CAP and SIMPER analyses identifying microbiome differences "saliva" vs. "plaque" and HC vs. SCC vs. SCC+chemo groups.

FIG. 3. Non-metric multi-dimensional scaling of the variables site (mucosa, dental plaque, tongue) and time (pre- and post-radiation therapy).

FIG. 8. Permutational MANOVA (PERMANOVA) comparing pre-RT with post RT.

FIG. 9. Permutational MANOVA (PERMANOVOA) comparing pre-RT with post RT (excluding antibiotics and chemotherapy subgroups).

FIG. 10. SIMPER analysis.

SUMMARY OF THE INVENTION

Figure 1:
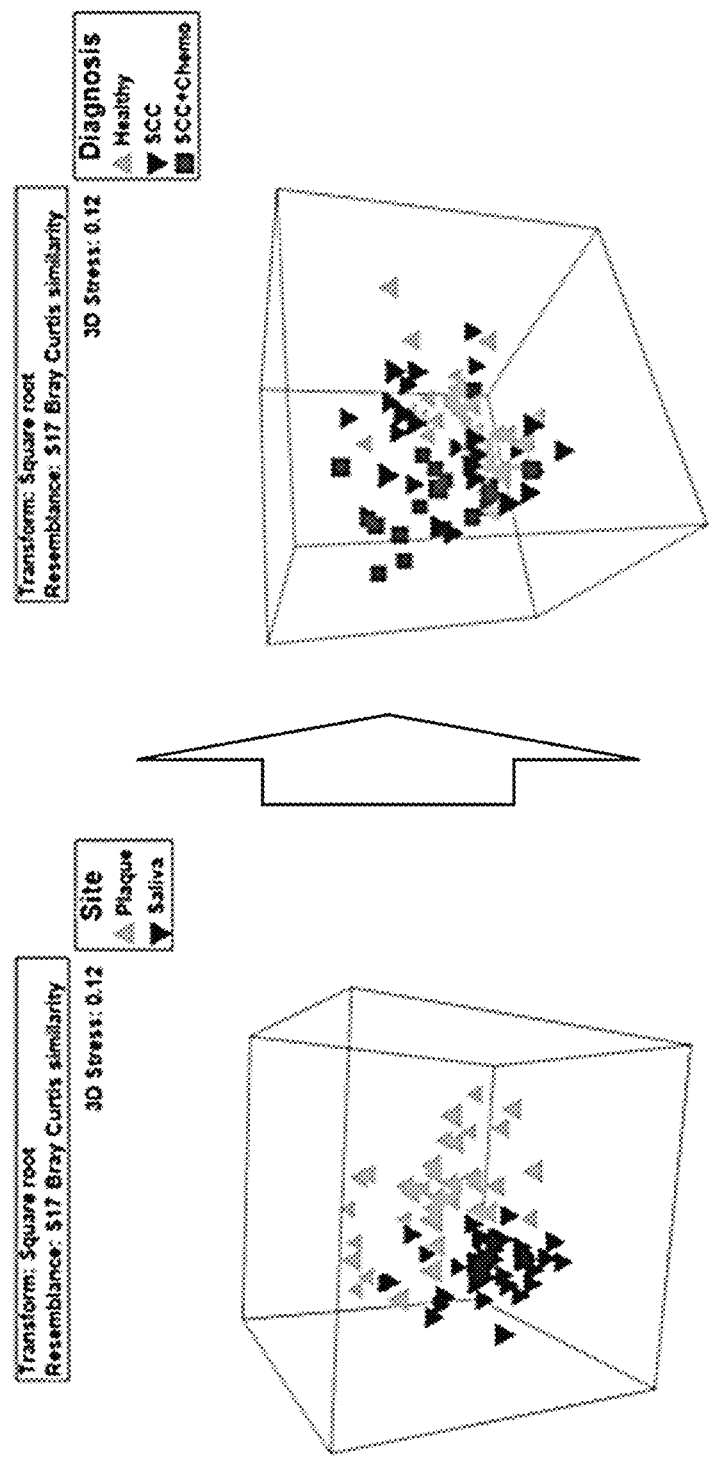
FIG. 1. Non-metric multi-dimensional scaling (nMDS) of "saliva" vs. "plaque"+chemo groups.

In one aspect the present invention provides a method of identifying a subject having an increased risk of developing oral complications associated with radiation therapy and/or chemotherapy, comprising: a) determining an oral microbiome signature of the subject; and b) comparing the microbiome signature of the subject with an oral microbiome profile correlated with oral complications associated with radiation therapy and/or chemotherapy, wherein an oral microbiome signature of the subject having similarity with the oral microbiome profile correlated with oral complications associated with radiation therapy and/or chemotherapy identifies the subject as having an increased risk of developing oral complications associated with radiation therapy and/or chemotherapy.

An additional aspect of this invention is a method of assessing a subject's risk of developing oral complications associated with radiation therapy and/or chemotherapy over time while receiving radiation therapy and/or chemotherapy, comprising: a) determining an oral microbiome signature of the subject prior to receiving radiation therapy and/or chemotherapy; b) determining an oral microbiome signature of the subject at one or more time points after initiation of radiation therapy and/or chemotherapy; and c) comparing the oral microbiome signatures obtained in steps (a) and (b) with an oral microbiome profile correlated with oral complications associated with radiation therapy and/or chemotherapy, wherein one or more of the microbiome signatures having similarity with the oral microbiome profile associated with radiation therapy and/or chemotherapy identifies the subject as having an increased risk of developing oral complications associated with radiation therapy and/or chemotherapy.

Further provided herein is a method of identifying a subject having an increased likelihood of a poor prognosis related to oral complications associated with radiation therapy and/or chemotherapy, comprising: a) determining an oral microbiome signature of the subject; and b) comparing the microbiome signature of the subject with an oral microbiome profile correlated with poor prognosis related to oral complications associated with radiation therapy and/or chemotherapy, wherein an oral microbiome signature having similarity with the oral microbiome profile correlated with poor prognosis related to oral complications associated with radiation therapy and/or chemotherapy identifies the subject as having an increased likelihood of a poor prognosis related to oral complications associated with radiation therapy and/or chemotherapy.

A method is also provided of monitoring a subject's response to treatment for oral complications associated with radiation therapy and/or chemotherapy, comprising: a) determining an oral microbiome signature of the subject prior to treatment for oral complications associated with radiation therapy and/or chemotherapy; b) determining an oral microbiome signature of the subject at one or more time points after initiation of treatment for oral complications associated with radiation therapy and/or chemotherapy; and c) comparing the oral microbiome signatures obtained in steps (a) and (b), wherein an oral microbiome signature determined after initiation of treatment having less similarity with an oral microbiome profile correlated with oral complications associated with radiation therapy and/or chemotherapy as compared with the oral microbiome signature determined prior to treatment identifies the subject as having a positive response to treatment, and an oral microbiome signature determined after initiation of treatment having more similarity with an oral microbiome profile correlated with oral complications associated with radiation therapy and/or chemotherapy as compared with the oral microbiome signature determined prior to treatment identifies the subject as having a negative response to treatment.

Another aspect of this invention is a method of guiding clinical decision making for a subject in need of radiation therapy and/or chemotherapy for a head and neck cancer, comprising: a) determining an oral microbiome signature of the subject prior to radiation therapy and/or chemotherapy for head and neck cancer; and c) comparing the oral microbiome signature with oral microbiome profiles correlated with different oral complications associated with radiation therapy and/or chemotherapy, wherein an oral microbiome signature having similarity with one or more oral microbiome profiles correlated with different oral complications associated with radiation therapy and/or chemotherapy guides the clinical decision making for the subject.

Furthermore, the present invention provides a method of identifying a subject having an increased risk of developing oral complications associated with radiation therapy and/or chemotherapy, comprising: a) correlating the presence of an oral microbiome profile with increased risk of developing oral complications associated with radiation therapy and/or chemotherapy; and b) detecting the oral microbiome profile of step (a) in the subject, thereby identifying the subject as having an increased risk of developing oral complications associated with radiation therapy and/or chemotherapy.

Additionally provided herein is a method of correlating an oral microbiome profile of a subject with oral complications associated with radiation therapy and/or chemotherapy, comprising: a) identifying a subject or population of subjects having oral complications associated with radiation and/or chemotherapy; b) determining the oral microbiome profile of the subject or of each of the subjects of the population of (a); and c) correlating the presence of the microbiome profile of step (b) with oral complications in the subject or population of subjects.

The present invention also provides a method of identifying an oral microbiome profile correlated with oral complications associated with radiation therapy and/or chemotherapy; comprising: a) identifying a subject having oral complications associated with radiation therapy and/or chemotherapy; b) detecting in a subject the presence of an oral microbiome profile; and c) correlating the presence of the oral microbiome profile of step (b) with oral complications associated with radiation therapy and/or chemotherapy, thereby identifying an oral microbiome profile correlated with oral complications associated with radiation therapy and/or chemotherapy.

The foregoing and other aspects of the present invention will now be described in more detail with respect to other embodiments described herein.

DETAILED DESCRIPTION OF THE INVENTION

For the purposes of promoting an understanding of the principles of the present invention, reference will now be made to particular embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the invention relates.

The present invention is based on the unexpected discovery that a subject's oral microbiome signature can be used to predict the subject's risk of having or developing oral complications associated with radiation therapy and/or chemotherapy for a head and neck cancer, as well as, e.g., monitor and guide treatment and/or establish a prognosis, among other uses. Accordingly, in one embodiment, the present invention provides a method of identifying a subject having an increased risk of developing oral complications associated with radiation therapy and/or chemotherapy, comprising: a) determining an oral microbiome signature of the subject; and b) comparing the microbiome signature of the subject with an oral microbiome profile correlated with oral complications associated with radiation therapy and/or chemotherapy, wherein an oral microbiome signature of the subject having similarity with the oral microbiome profile correlated with oral complications associated with radiation therapy and/or chemotherapy identifies the subject as having an increased risk of developing oral complications associated with radiation therapy and/or chemotherapy.

An additional aspect of this invention is a method of assessing a subject's risk of developing oral complications associated with radiation therapy and/or chemotherapy over time while receiving radiation therapy and/or chemotherapy, comprising: a) determining an oral microbiome signature of the subject prior to receiving radiation therapy and/or chemotherapy; b) determining an oral microbiome signature of the subject at one or more time points after initiation of radiation therapy and/or chemotherapy; and c) comparing the oral microbiome signatures obtained in steps (a) and (b) with an oral microbiome profile correlated with oral complications associated with radiation therapy and/or chemotherapy, wherein one or more of the microbiome signatures having similarity with the oral microbiome profile associated with radiation therapy and/or chemotherapy identifies the subject as having an increased risk of developing oral complications associated with radiation therapy and/or chemotherapy.

Further provided herein is a method of identifying a subject having an increased likelihood of a poor prognosis related to oral complications associated with radiation therapy and/or chemotherapy, comprising: a) determining an oral microbiome signature of the subject; and b) comparing the microbiome signature of the subject with an oral microbiome profile correlated with poor prognosis related to oral complications associated with radiation therapy and/or chemotherapy, wherein an oral microbiome signature having similarity with the oral microbiome profile correlated with poor prognosis related to oral complications associated with radiation therapy and/or chemotherapy identifies the subject as having an increased likelihood of a poor prognosis related to oral complications associated with radiation therapy and/or chemotherapy.

A method is also provided of monitoring a subject's response to treatment for oral complications associated with radiation therapy and/or chemotherapy, comprising: a) determining an oral microbiome signature of the subject prior to treatment for oral complications associated with radiation therapy and/or chemotherapy; b) determining an oral microbiome signature of the subject at one or more time points after initiation of treatment for oral complications associated with radiation therapy and/or chemotherapy; and c) comparing the oral microbiome signatures obtained in steps (a) and (b), wherein an oral microbiome signature determined after initiation of treatment having less similarity with an oral microbiome profile correlated with oral complications associated with radiation therapy and/or chemotherapy as compared with the oral microbiome signature determined prior to treatment identifies the subject as having a positive response to treatment, and an oral microbiome signature determined after initiation of treatment having more similarity with an oral microbiome profile correlated with oral complications associated with radiation therapy and/or chemotherapy as compared with the oral microbiome signature determined prior to treatment identifies the subject as having a negative response to treatment.

Another aspect of this invention is a method of guiding clinical decision making for a subject in need of radiation therapy and/or chemotherapy for a head and neck cancer, comprising: a) determining an oral microbiome signature of the subject prior to radiation therapy and/or chemotherapy for head and neck cancer; and c) comparing the oral microbiome signature with oral microbiome profiles correlated with different oral complications associated with radiation therapy and/or chemotherapy, wherein an oral microbiome signature having similarity with one or more oral microbiome profiles correlated with different oral complications associated with radiation therapy and/or chemotherapy guides the clinical decision making for the subject.

Furthermore, the present invention provides a method of identifying a subject having an increased risk of developing oral complications associated with radiation therapy and/or chemotherapy, comprising: a) correlating the presence of an oral microbiome profile with increased risk of developing oral complications associated with radiation therapy and/or chemotherapy; and b) detecting the oral microbiome profile of step (a) in the subject, thereby identifying the subject as having an increased risk of developing oral complications associated with radiation therapy and/or chemotherapy.

Additionally provided herein is a method of correlating an oral microbiome profile of a subject with oral complications associated with radiation therapy and/or chemotherapy, comprising: a) identifying a subject or population of subjects having oral complications associated with radiation and/or chemotherapy; b) determining the oral microbiome profile of the subject or of each of the subjects of the population of (a); and c) correlating the presence of the microbiome profile of step (b) with oral complications in the subject or population of subjects.

The present invention also provides a method of identifying an oral microbiome profile correlated with oral complications associated with radiation therapy and/or chemotherapy; comprising: a) identifying a subject having oral complications associated with radiation therapy and/or chemotherapy; b) detecting in a subject the presence of an oral microbiome profile; and c) correlating the presence of the oral microbiome profile of step (b) with oral complications associated with radiation therapy and/or chemotherapy, thereby identifying an oral microbiome profile correlated with oral complications associated with radiation therapy and/or chemotherapy.

The methods of this invention can further comprise the step of treating the subject for oral complications associated with radiation therapy and/or chemotherapy.

In some embodiments, the oral complication is caries and the oral microbiome signature of the subject has similarity with the oral microbiome profile correlated with caries, thereby guiding the clinical decision making for the subject to be treatment for caries.

In some embodiments, the oral complication is periodontitis and the oral microbiome signature of the subject has similarity with the oral microbiome profile correlated with periodontitis, thereby guiding the clinical decision making for the subject to be treatment for periodontitis.

In some embodiments, the oral complication is xerostomia and the oral microbiome signature of the subject has similarity with the oral microbiome profile correlated with xerostomia, thereby guiding the clinical decision making for the subject to be treatment for xerostomia.

In some embodiments, the oral complication is oral mucositis and the oral microbiome signature of the subject has similarity with the oral microbiome profile correlated with oral mucositis, thereby guiding the clinical decision making for the subject to be treatment for oral mucositis.

The methods of this invention can further comprise the step of treating the subject for the oral complication. Exemplary treatment protocols for the various oral complications associated with cancer treatment are described herein.

The methods of this invention can be carried out according to the protocols set forth in the Examples section provided herein and according to protocols known in the art. For example, an oral microbiome signature of a subject of this invention can be obtained or produced by analyzing an oral sample obtained from the subject (e.g., saliva, cells from the subject's oral cavity, etc.) for the type and quantity of various groups and/or species of bacteria. Such analysis can be at the nucleic acid level, protein level and/or whole organism level, according to methods known in the art.

An oral microbiome profile that is correlated with oral complications associated with radiation therapy and/or chemotherapy can be obtained or produced by analyzing an oral sample obtained from each subject in a population of subjects for the type and quantity of various groups and/or species of bacteria, wherein a population of subjects can be a population of subjects that are not undergoing radiation therapy and/or chemotherapy (e.g., a control) and another population of subjects can be a population of subjects that have been and/or are currently undergoing radiation therapy and/or chemotherapy. A control of this invention can also be a subject of this invention prior to undergoing radiation therapy and/or chemotherapy. Such analysis can be at the nucleic acid level, protein level and/or whole organism level, according to methods known in the art.

The oral microbiome profile would include a description of the type and/or quantity of various species of bacteria that are found in an oral sample in the subjects of each population analyzed. Thus, an oral microbiome profile is produced for control subjects and an oral microbiome profile is produced for subjects that have been and/or are currently undergoing radiation therapy and/or chemotherapy.

An oral microbiome profile can be correlated with oral complications of radiation therapy and/or chemotherapy by determining an oral microbiome profile of a population of subjects, wherein each population of subjects is defined as having an oral complication of radiation therapy and/or chemotherapy (e.g., a population of subjects having caries, a population of subjects having periodontitis, a population of subjects having xerostomia and/or a population of subjects having oral mucositis). The oral microbiome profile (i.e., the type and/or quantity of various groups and/or species of bacteria) can be statistically correlated with the presence of the particular oral complication of a given population of subjects, thereby identifying an oral microbiome profile correlated with a particular oral complication.

The oral microbiome signature determined for the subject of this invention can be compared with an oral microbiome profile correlated with any of the various oral complications and the subject can be defined as having an increased risk of having or developing an oral complication if the subject's oral microbiome signature is similar to the oral microbiome profile correlated with any of the various oral complications of this invention.

It should be noted in certain embodiments that although a control profile or correlative profile for comparison would generally be obtained by testing an appropriate population of subjects, the methods of this invention do not necessarily involve carrying out active tests on such populations but would generally involve a comparison of profiles that have been determined previously.

Thus, the methods of this invention can be used to identify and/or monitor a subject for oral complications that may benefit from treatment, which can be prior to, during and/or following radiation therapy and/or chemotherapy. The treatment of such subjects can also be monitored and/or modified according to the methods described herein. For example, the oral microbiome signature of a subject can be analyzed over time and if the oral microbiome signature is changing to be more similar to the oral microbiome profile of a normal or control subject in response to treatment or changing to be more similar to an oral microbiome profile correlated with any of the various oral complications of radiation therapy and/or chemotherapy, treatment can be modified accordingly.

It is understood that although the methods of this invention can be used in isolation, they can also form a part of a multimarker approach for diagnosing and/or identifying risk of oral complications of radiation therapy and/or chemotherapy. Thus, the methods of the present invention might not only be used in place of a measurement of other biomarkers, but might also be used in combination, or in addition to the measurement or analysis of one or more other markers or biomarkers known to be associated with oral complications of radiation therapy and/or chemotherapy.

In some embodiments, the oral microbiome profile correlated with oral complications associated with radiation therapy and/or chemotherapy comprises microbial species listed in Table 6.

Definitions

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. A subject of this invention can be any subject that is susceptible to oral complications associated with radiation therapy and/or chemotherapy, and in particular embodiments, the subject of this invention is a human subject.

A "subject in need thereof" or "a subject in need of" is a subject known to have, or is suspected of having or developing oral complications associated with radiation therapy and/or chemotherapy. In particular embodiments, the subject is in need of, is scheduled for and/or is planning to undergo radiation and/or chemotherapy and/or other cancer treatment.

As used herein, "microbiome" refers to the population of microorganisms that are present in a particular environment, such as the gut or digestive system, the urogenital tract, the mouth, the oral cavity, and the like. A microbiome is a microbial population defined by the diversity as well as the relative amounts of bacteria that compose a particular microbiome.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

Non-limiting examples of treatments of the disorders described in the present invention include the following.

Caries (radiation caries), also known as cavities, are permanently damaged areas in teeth that develop into tiny holes. Treatments for caries include fluoride, fillings, and/or crowns. Severe cases may need a root canal or extraction.

Periodontitis is a serious gum infection that damages gums and can destroy the jawbone. Treatments for periodontitis include professionally cleaning the pockets around teeth to prevent damage to surrounding bone. Advanced cases may require surgery, such as flap surgery (pocket reduction surgery).

Xerostomia, also known as dry mouth, occurs when the salivary glands fail to produce enough saliva to moisten and cleanse the mouth. A doctor may prescribe an oral rinse to restore mouth moisture and/or prescribe a medication such as Salagen, a medication that boosts saliva production. Other possible treatments include chewing sugar-free gum, limiting caffeine intake, stopping all tobacco use (if applicable), drinking water regularly, using an over-the-counter saliva substitute, and/or sleeping with a humidifier.

Oral mucositis is inflammation of the mucous membrane in the mouth. For those suffering from oral mucositis, it is very important to have a good oral hygiene routine. Other self-care treatments include avoiding certain foods and drinks, sucking on ice cubes or ice chips, taking painkillers in the form of a mouth rinse, gel or spray, or taking palifermin.

Neurotoxicity is damage to the peripheral nervous system. The treatment approach to neurotoxicity is elimination or reduction of the toxic substance and therapy to relieve symptoms and/or provide support. Treatment may also involve avoiding air, food and/or water pollutants. Some examples of therapies used in the treatment of neurotoxicity include massage, exercise and/or immune modulation.

Bleeding of the gums can be controlled by applying pressure to the area with a cold compress and/or rinsing with salt water or hydrogen peroxide to keep the area clean.

Trismus, also known as lockjaw, is a reduced opening of the jaws (limited jaw range of motion). Treatment requires treating the underlying condition with dental treatments, physical therapy, and/or passive range of motion devices. Additionally, control of symptoms with pain medications (e.g., NSAIDs), muscle relaxants, and/or warm compresses may be used.

Osteonecrosis, which is also called avascular necrosis or aseptic necrosis, is the death of bone cells due to decreased blood flow. Often, treatment starts with pain medications. Patients whose osteonecrosis is getting worse may need a procedure called core decompression. It removes a piece (core) of bone from the affected area, to try to improve blood flow. More advanced cases may need an osteotomy. Another surgery option for advanced cases is bone grafting.

Infection treatments may include antibiotics, antifungal, and/or antiviral medications. Oral cryotherapy (e.g., ice in the mouth) can also be employed prior to, during and/or following radiation therapy and/or chemotherapy.

Alteration in taste can be a side effect of cancer therapy. There is no one solution for those experiencing taste alterations. Finding foods that taste appealing may be a process of trial and error. There are no medications that address taste changes. However, some studies have suggested that deficiencies in zinc, copper, nickel, niacin and vitamin A may contribute to taste changes and addressing these deficiencies may be helpful in addressing the taste alteration.

Patients receiving aggressive cancer therapies typically need aggressive nutrition management to help with nutritional compromise.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition such as an oral complication associated with radiation therapy and/or chemotherapy. In some embodiments, the term "prevent" refers to the ability to keep a condition such as an oral complication associated with radiation therapy and/or chemotherapy from happening or existing as well as to diminish or delay onset. In some embodiments, the term "treating" refers to the caring for, or dealing with, a condition such as an oral complication associated with radiation therapy and/or chemotherapy.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

A composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

By "parenteral" is meant intravenous, subcutaneous or intramuscular administration. In the methods of the present invention, the composition or compound may be administered alone, simultaneously with one or more other compounds, or the composition and/or compounds may be administered sequentially, in either order. It will be appreciated that the actual method and order of administration will vary according to, inter alia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein.

In prophylactic applications, pharmaceutical compositions or medicaments are administered to a subject susceptible to, or otherwise at risk of, occlusion or narrowing of an artery and/or its branches and/or a disease, disturbance and/or pathological condition of an artery and/or its branches in an amount sufficient to eliminate or reduce the risk, lessen the severity, or delay the onset, including biochemical, histologic and/or physiologic symptoms. In therapeutic applications, compositions or medicants are administered to a subject suspected of, or already having, occlusion or narrowing of an artery and/or its branches and/or has had or is having a disease, disturbance and/or pathological condition of an artery and/or its branches in an amount sufficient to treat, or at least partially reduce or arrest, the symptoms (biochemical, histologic and/or physiological). An amount adequate to accomplish therapeutic or prophylactic treatment is defined as an effective amount or a therapeutically or prophylactically effective dose. In either prophylactic or therapeutic regimens, compounds and/or compositions of the present invention can be administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the compositions of this invention will be determined by the age, weight and condition or severity of disease or disorder of the subject.

Generally, dosing (e.g., an administration) can be one or more times daily, or less frequently, such as once a day, once a week, once a month, once a year, to once in a decade, etc. and may be in conjunction with other compositions as described herein.

The dosage and frequency of administration can vary depending on whether the treatment is prophylactic or therapeutic. In prophylactic applications, a relatively low dosage can be administered at relatively infrequent intervals over a long period of time. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The terms "increased risk" and "decreased risk" as used herein define the level of risk that a subject has of having or developing oral complications as described herein, as compared to a control subject.

A sample of this invention can be cells, tissue and/or fluid (e.g., saliva, buccal swab, salivary gland tissue, etc.) from the oral cavity of a subject, as well as any other biological material from the subject that can be used to identify the oral microbiome signature of the subject.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is more particularly described in the following examples that are intended as illustrative only since numerous modifications and variations therein will be apparent to those skilled in the art.

EXAMPLES

Example 1. Use of Oral Microbiomic Signatures to Predict Risk and Monitor the Development and Response to Treatment of Oral Complications of Head and Neck Cancer Patients Undergoing Radiation and/or Chemo-Therapy The purpose of this invention is to use oral microbiome signatures as biomarkers for the prediction of risk, progression, and/or response to treatment for oral complications associated with cancer therapy (e.g., radiation therapy and/or chemotherapy). Oral complications include but are not limited to the development of caries, periodontitis, xerostomia and oral mucositis. Oral microbiome signatures can be used as biomarkers and defined by the relative proportions and/or absolute abundance and/or associated bacterial gene expression.

Old means lack the capability and precision of detecting specific biomarkers that would have a predictive power for oral complications and that would define which patients are more at risk to develop oral complications in which the oral microbiome plays a role.

We are designing a test using Next Generation Sequencing (NGS) technology (i.e., HOMINGS) customized to a panel of oral species and a qRT-PCR assay adapted for this panel of species. In addition, bacterial RNA gene expression will be determined using qRT-PCR methods following NGS RNASeq experiments that will identify composite signature (s) associated with or predictive of oral complications. The composite test measuring both relative and absolute abundance of a panel of species, along with mRNA expression profiles associated with these species, will be used to monitor changes in microbiomic marker signatures before, during and after cancer therapy. The test will be used to better manage cancer patients in a tailored and personalized manner.

Current results obtained by HOMINGS were analyzed in PRIMER software. Discriminant analysis of Canonical Analysis of Principle coordinates (CAP) of oral microbiome profiles indicated that pre-radiation therapy samples were correctly classified with 87.5% accuracy, while post-radiation therapy samples were classified with 83.3% accuracy. Further studies will be conducted to establish correlations with clinical outcomes in order to devise an algorithm for personalized oral care applied to head and neck (H&N) cancer patients undergoing cancer therapy. Certain bacterial subprofiles and expression pattern correlates will yield higher and clinically acceptable predictive value to identify patients at risk. Thus, the microbiome signature will provide a prognostic value/risk estimate for developing oral complications such as caries, periodontitis or other disorders.

Correlations of this invention will be made e.g., using relative proportions and absolute abundance of a select panel of bacterial species; bacterial mRNA expression profiles associated with abundance changes of the select panel of bacterial species constituting a signature predictive of the oral complication associated with cancer therapy; human oral mucosa genetics (mutations, indels, single nucleotide polymorphisms, copy number variations) and/or mRNA expression profiles correlating with the select panel of bacterial species as a specific host-response, thereby constituting a signature predictive of the oral complication associated with cancer therapy; (surrogate) blood/serum/plasma markers relevant of a host-response associated with profiles of select panel of bacterial species, thereby predictive of the oral complication associated with cancer therapy; an outcome prediction statistical model applicable in the clinic.

Example 2. Oral Microbiome Shifts in Head and Neck Cancer

Objective: Cancer therapy in patients with head and neck cancer can lead to transient or chronic oral complications. Our goal was to characterize the oral microbiome, at the species level, in patients with oral squamous cell carcinoma (OSCC) undergoing induction chemotherapy.

Methods: A cross-sectional design was used consisting of three groups: healthy controls (HC; n=17), subjects with OSCC (OSCC; n=13), or OSCC+induction chemotherapy (OSCC-Ch; n=9). Human Oral Microbiome Identification using Next Generation Sequencing (HOMINGS) of bacterial DNA isolated from dental plaque and saliva was used to determine the relative abundance of nearly 600 oral species. Simpson and Shannon indices of diversity were determined for each subject and differences between the groups were tested by two-way ANOVA (post hoc Tukey HSD) in XLSTAT. Differences between the groups based on Bray-Curtis similarity matrices were analyzed by SIMPER, two-way PERMANOVA (fixed factors: oral site, group), and CAP in PRIMER v6.

Results: Overall, 465 species were detected across subjects. The range of species detected per subject was 44 to 215 [mean (SD), 115 (42)] in dental plaque and 73 to 250 [mean (SD), 144 (38)] in saliva. There was a significant difference between the groups for both Simpson and Shannon indices of diversity, namely, pairwise comparisons HC vs. OSCC and OSCC vs. OSCC-Ch [ANOVA: p<0.05, no oral site by group effect]. A significant difference between the groups (HC, OSCC, and OSCC-Ch) based on Bray-Curtis similarity matrices was found for all pairwise comparisons [PERMANOVA: overall P(perm)=0.0001, pairwise P(perm)<0.01, no oral site by group effect]. Examination of CAP and SIMPER results suggested that several *Prevotella* spp. correlated with segregation of the three groups (CAP: r>0.5).

Conclusion: Oral bacterial communities may undergo significant shifts in chemotherapy-treated OSCC patients. Investigation of these changes at the species level in larger cohorts may provide further insights on the development of oral complications.

Example 3. Oral Microbiome in Head and Neck Cancer: A Longitudinal Study

Objective: High-dose radiation therapy may lead to oral complications in head and neck cancer patients. Our objective was to characterize oral microbiome, at the species level, at baseline and six months following radiation therapy.

Methods: Human Oral Microbiome Identification using Next Generation Sequencing (HOMINGS) of bacterial DNA was used to determine the relative abundance of nearly 600 oral species. Bacterial DNA was isolated from buccal mucosa, dental plaque and tongue samples of eight subjects with oral squamous cell carcinoma at baseline and six months following radiation therapy. Two subjects had been treated with induction chemotherapy and three with antibiotics, within two weeks of sampling (i.e., baseline status). Differences between the groups pre- and post-radiation therapy were analyzed by SIMPER, PERMANOVA and CAP in PRIMER v6. The analytical design for PERMANOVA was: Time (fixed: pre- and post-radiation therapy), Oral Site (fixed: buccal mucosa, dental plaque, tongue), Baseline Status (random and nested in Oral Site), Subject (random and nested in Oral Site and Baseline Status).

Results: The number of species detected per subject ranged from 61 to 228 [mean (SD), 110 (41)] in pre-radiation group (overall 387 species) and 40 to 212 [mean (SD), 106 (38)] in post-radiation group (overall 362 species). A significant difference was found between pre- and post-radiation groups [PERMANOVA: P(perm)=0.0227, P(MC)=0.0024, no interactions]. CAP and SIMPER results suggested that several *Prevotella* spp. correlated with changes associated with radiation therapy (CAP: r>0.5). The difference between pre- and post-radiation groups was still significant after limiting the analysis to patients, neither exposed to chemotherapy nor antibiotics at baseline [PERMANOVA: P(perm)=0.014, P(MC)=0.019, no interaction].

Conclusion: Radiation therapy in head and neck cancer patients likely incurs significant long term changes in the oral microbiome, along with other treatments, potentially increasing the risk for oral complications. Confirmation with a large well-stratified cohort and multiple time points is warranted.

Example 4. Oral Microbiome Shifts in Head and Neck Cancer

Head and neck cancer represents approximately 3% of all cancers and affect men twice as often as women. Head and neck cancer is more often diagnosed in patients over the age of 50. Over 90% of cancers known collectively as "head and neck cancers" originate in squamous cells and are referred to as squamous cell carcinomas. Cancer therapy in patients with head and neck cancer can lead to transient or chronic oral complications. Approximately 700 bacterial species are estimated to reside in human oral cavity. Oral microbiome changes may be associated with oral complications.

Cancer therapy in patients with head and neck cancer can lead to transient or chronic oral complications. Our goal was to characterize the oral microbiome, at the species level, in patients with oral squamous cell carcinoma (OSCC).

Human Methods: A cross-sectional design was used consisting of three groups: healthy controls (HC; n=17), subjects with OSCC (OSCC; n=13), or OSCC+chemotherapy (OSCC-Ch; n=9). Human Oral Microbiome Identification using Next Generation Sequencing (HOMINGS) of bacterial DNA isolated from dental plaque and saliva was used to determine the relative abundance of nearly 600 oral species. Simpson and Shannon indices of diversity were determined for each subject and differences between the groups were tested by two-way ANOVA (post hoc Tukey HSD). Differences between the groups based on Bray-Curtis similarity matrices were analyzed by SIMPER, two-way PERMANOVA (fixed factors: oral site, group), and CAP.

Overall, 465 species were detected across subjects. The range of species detected per subject was 44 to 215 [mean (SD), 115 (42)] in dental plaque and 73 to 250 [mean (SD), 144 (38)] in saliva. There was a significant difference between the groups for both Simpson and Shannon indices of diversity, namely, pairwise comparisons HC vs. OSCC and OSCC vs. OSCC-Ch [ANOVA: p<0.05, no oral site by group effect]. A significant difference between the groups (HC, OSCC, and OSCC-Ch) based on Bray-Curtis similarity matrices was found for all pairwise comparisons [PERMANOVA: overall P(perm)=0.0001, pairwise P(perm) <0.01, no oral site by group effect]. Examination of CAP and SIMPER results suggested that several *Prevotella* spp. correlated with segregation of the three groups (CAP: r>0.5).

Table 1 shows the number of species detected by HOMINGS.

Table 2 shows the alpha diversity analysis of HC vs. SCC vs. SCC+chemo groups.

Non metric Multi-Dimensional Scaling (nMDS) of "saliva" vs. "plaque" and HC vs. SCC vs. SCC+Chemo groups are shown in FIG. 1. Permutational MANOVA (PERMANOVA) comparing "saliva" vs. "plaque" and HC vs. SCC vs. SCC+Chemo groups is shown in Table 3.

Post-PERMANOVA CAP and SIMPER analyses identifying microbiome differences "saliva" vs. "plaque" and HC vs. SCC vs. SCC+Chemo groups are shown in FIG. 2 and Table 4.

Oral bacterial communities may undergo significant shifts in OSCC patients. Investigation of these changes at the species level in larger cohorts can provide further insights on the development of oral complications.

Example 5. Oral Microbiome in Head and Neck Cancer: A Longitudinal Study

Head and neck cancer represents approximately 3% of all cancers and affects men twice as often as women. Head and neck cancer is more often diagnosed in patients over the age of 50. Over 90% of cancers known collectively as "head and neck cancers" originate in squamous cells and are referred to as squamous cell carcinomas. Cancer therapy in patients with head and neck cancer can lead to transient or chronic oral complications. Approximately 700 bacterial species are estimated to reside in human oral cavity. Oral microbiome changes may be associated with oral complications.

High-dose radiation therapy may lead to oral complications in head and neck cancer patients. Our objective was to characterize the oral microbiome, at the species level, at baseline and six months following radiation therapy.

Human Oral Microbiome Identification using Next Generation Sequencing (HOMINGS) of bacterial DNA was used to determine the relative abundance of nearly 600 oral species. Bacterial DNA was isolated from buccal mucosa, dental plaque and tongue samples of 8 subjects with oral squamous cell carcinoma at baseline and six months following radiation therapy. Two subjects had been treated with chemotherapy and 3 with antibiotics, within two weeks of sampling (i.e., baseline status). Differences between the groups pre- and post-radiation therapy were analyzed by SIMPER, PERMANOVA and CAP in Primer v6. The analytical design for PERMANOVA was: Time (fixed: pre- and post-radiation therapy), Oral Site (fixed: buccal mucosa, dental plaque, tongue), Baseline Status (random and nested in Oral Site), Subject (random and nested in Oral Site and Baseline Status).

The number of species detected per subject ranged from 61 to 228 [mean (SD), 110 (41)] in pre-radiation group (overall 387 species) and 40 to 212 [mean (SD), 106 (38)] in post-radiation group (overall 362 species). A significant difference was found between pre- and post-radiation groups [PERMANOVA: P(perm)=0.0227; P(MC)=0.0024, no interactions]. CAP and SIMPER results suggested that several *Prevotella* spp. correlated with changes associated with radiation therapy (CAP: r>0.5). The difference between pre- and post-radiation groups was still significant after limiting the analysis to patients, neither exposed to chemotherapy nor antibiotics at baseline [PERMANOVA: P(perm)=0.14; P(MC)=0.019, no interaction].

Table 5 shows the number of species detected by HOMINGS.

FIG. 3 shows non-metric multi-dimensional scaling of the variables site (buccal mucosa, dental plaque, tongue) and time (pre- and post-radiation therapy). Permutational MANOVA (PERMANOVA) comparing pre-RT with post-RT is shown in FIG. 8.

Permutational MANOVA (PERMANOVA) comparing pre-RT with post-RT (excluding antibiotics and chemotherapy subgroups) is shown in FIG. 9.

Figure 4:
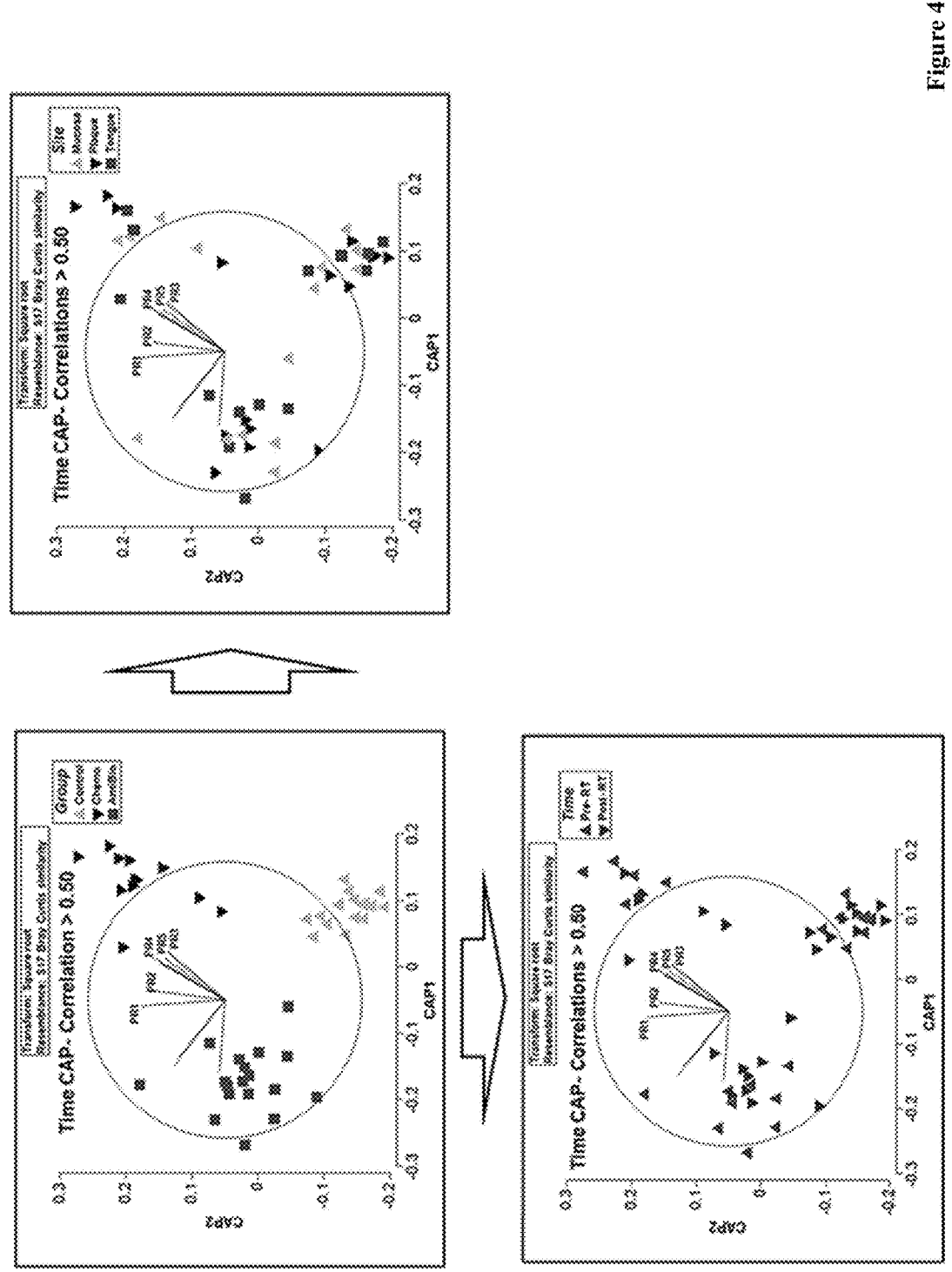
FIG. 4. Post-PERMANOVA CAP and SIMPER analyses suggest that differences between pre- and post-RT groups involve changes in relative abundance of many oral species including several *Prevotella* spp.

Post-PERMANOVA CAP and SIMPER analyses suggest that differences between pre- and post-RT groups involve changes in relative abundance of many oral species including several *Prevotella* spp., as shown in FIG. 4 and FIG. 10.

Radiation therapy in the head and neck cancer patients can incur significant long-term changes in the oral microbiome, along with other treatments, potentially increasing the risk for oral complications. Confirmation with a large well-stratified cohort and multiple time points is warranted.

Example 6. Oral Microbiome OraRad Data

Methodology The methodology for statistical analysis employed was as follows:

Two analyses were performed based on relative abundance data obtained by HOMINGS. In the first, the Baseline (BL) data were compared to the 6-months post-cancer treatment (P6) data. This analysis contained 43 pre- and post-matching samples. Sample sites were from buccal mucosa, supragingival dental plaque, tongue surfaces and saliva. In the second analysis, P6 data were compared to 18-months post-cancer treatment (P18) data. This analysis contained 28 pre- and post-matching samples. Both analyses were performed identically. For ease of description, the BL to P6 analysis only is described below, as the same procedure was also applied to the P6 to P18 analysis.

Also, two different sets of caries disease-associated species were used. The first set contained specifically named caries disease-associated species and caries-free associated species described in Tanner A C R et al. "Understanding Caries From the Oral Microbiome Perspective" *Calif Dent Assoc J.* 2016; 44(7): 437-446 (2016), but excluded all unspecified species represented on HOMINGS platform contained within specifically named genera. The subset of "Species Only" analyzed corresponding to n=46 species identified by species probes on HOMINGS (see list p.3 below). The second set of species included known species contained within the specifically named genera of the n=46 species, i.e., corresponding to n=205 species identified by HOMINGS species probes ("Species+Genera" analysis). This second larger subset was used to determine whether a change could also be observed more broadly within a genus.

Four unique analyses were thus performed:

Named Species Only: 1) BL vs. P6 and 2) P6 vs. P18.

Named Species+Other known Species of same genera: 3) BL vs. P6 and 4) P6 vs. P18.

All patient samples were used for which there were corresponding BL and P6 HOMINGS data. All patients were not exposed to antibiotic effects within at least two weeks prior to sampling. The patients did not receive "induction" chemotherapy at baseline, but did receive chemotherapy concurrent with their radiation therapy.

Only species probe "hits" (matching sequence reads counts) were used to determine relative proportions for all species of the two subsets and all patient samples. No genus probe hit (corresponding to sequence reads that were no matched to species probes) were used in the analysis. However, the denominator used to calculate relative proportions was the sum of the species probes total hits plus the genus probe total hits for that corresponding patient sample. The individual species relative proportions determined constituted the raw data for all following steps.

The following outputs were determined for each patient sample in the analysis BL vs. P6, for example:

(i) A net health or net disease starting point was calculated from the BL and P6 samples from the same patient Example If the relative proportion of total caries-associated species at BL was 3.5% and that of caries-free was 20.1%, there would be a net negative value of −16.6% (3.5 minus 20.1), thereby defining a healthy status "h."

If the relative proportion of total caries-associated species at P6 was 42.4% and that of caries-free was 1% there would be a net positive value of 41.4%, thereby defining a "disease" endpoint status "d."

(ii) An Endpoint Effect was tested for statistical significance by counting how many "d" at BL remained "d" or became "h" at P6, how many "h" at BL remained "h" or became "d" at P6. An endpoint contingency table was established to conduct a McNemar test with continuity correction as in the example below (n=43 samples, n=13 patients, "Species+Genera" analysis shown in Table 7):

| Endpoint contingency table | | |
|---|---|---|
| BL⇨P6 | Health | Disease |
| Health | 3 | 17 |
| Disease | 2 | 21 |

(iii) A Directional Effect was also evaluated. In this case, if the change in relative proportions did not change the endpoint status, e.g., a "d" at baseline remained "d" at P6, but the relative proportion for disease associated species was reduced (i.e., direction moving towards "health" status), it was counted as an "h" healthier directional status. Again, a directional contingency table was established to conduct a McNemar test with continuity correction:

| Directional contingency table | | |
|---|---|---|
| BL⇨P6 | Health | Disease |
| Health | 3 | 17 |
| Disease | 8 | 15 |

In this example, while the Endpoint contingency table showed 2 "d" at BL to "h" at P6 changes, the Directional contingency table shows 8 "d" at BL that moved towards "h," meaning that 6 out of the 21 patients that had a "d" to "d" endpoint status, saw a reduction in overall counts for caries disease-associated species and where thus counted as "d" to "h," leaving 15 "d" to "d."

While in this example, the McNemar test for Endpoint Effect yielded p=0.00132, the test yielded p=0.1096 for the Directional Effect.

Figure 5:
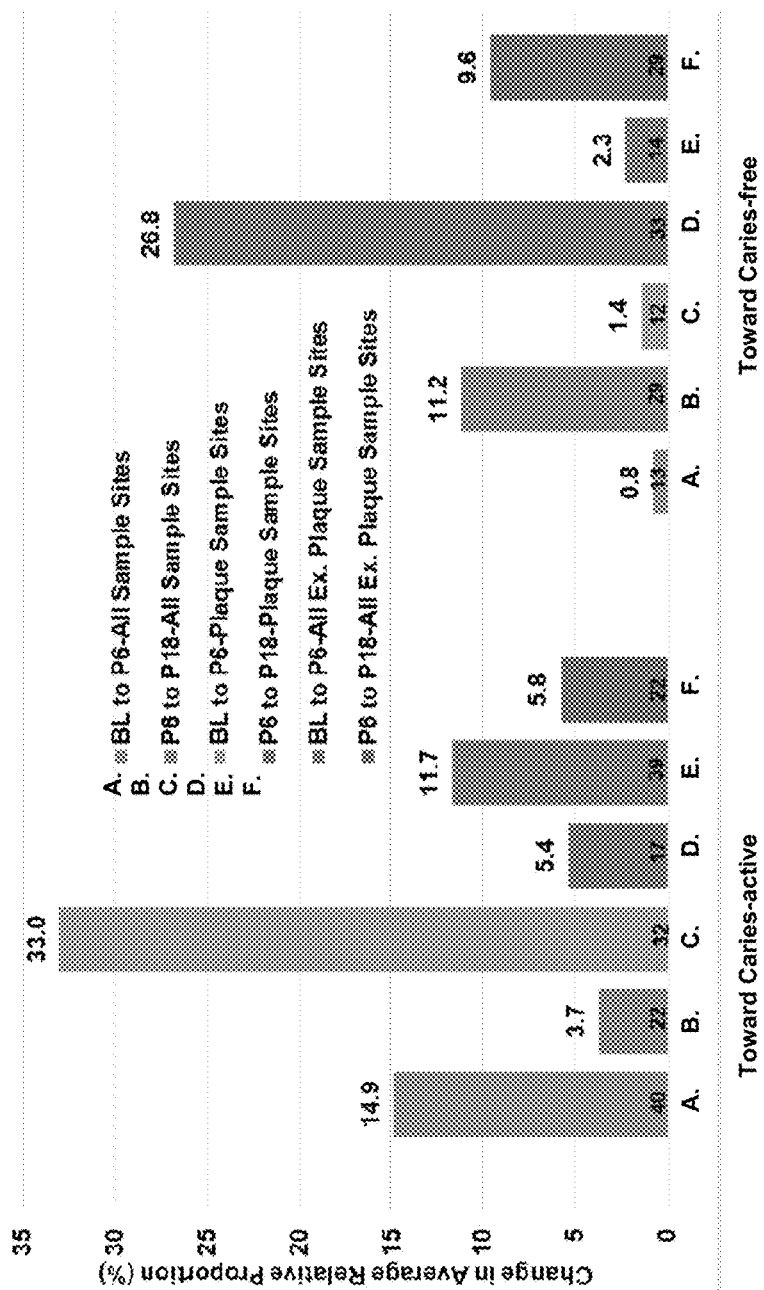
FIG. 5. Change in Average Relative Proportion (%) from Baseline (BL) to P6 and P6 to P18 per HOMINGS for "Caries-free" and "Caries-active" associated species (Tanner et al. 2016). Numbers at bottom of bars represent the number of species detected; *S. sanguinis* was considered "caries-free" associated species; all patients had chemotherapy concurrent to radiation therapy, were antibiotic free for at least 2 weeks prior to sampling, and did not receive induction chemotherapy.
Figure 6:
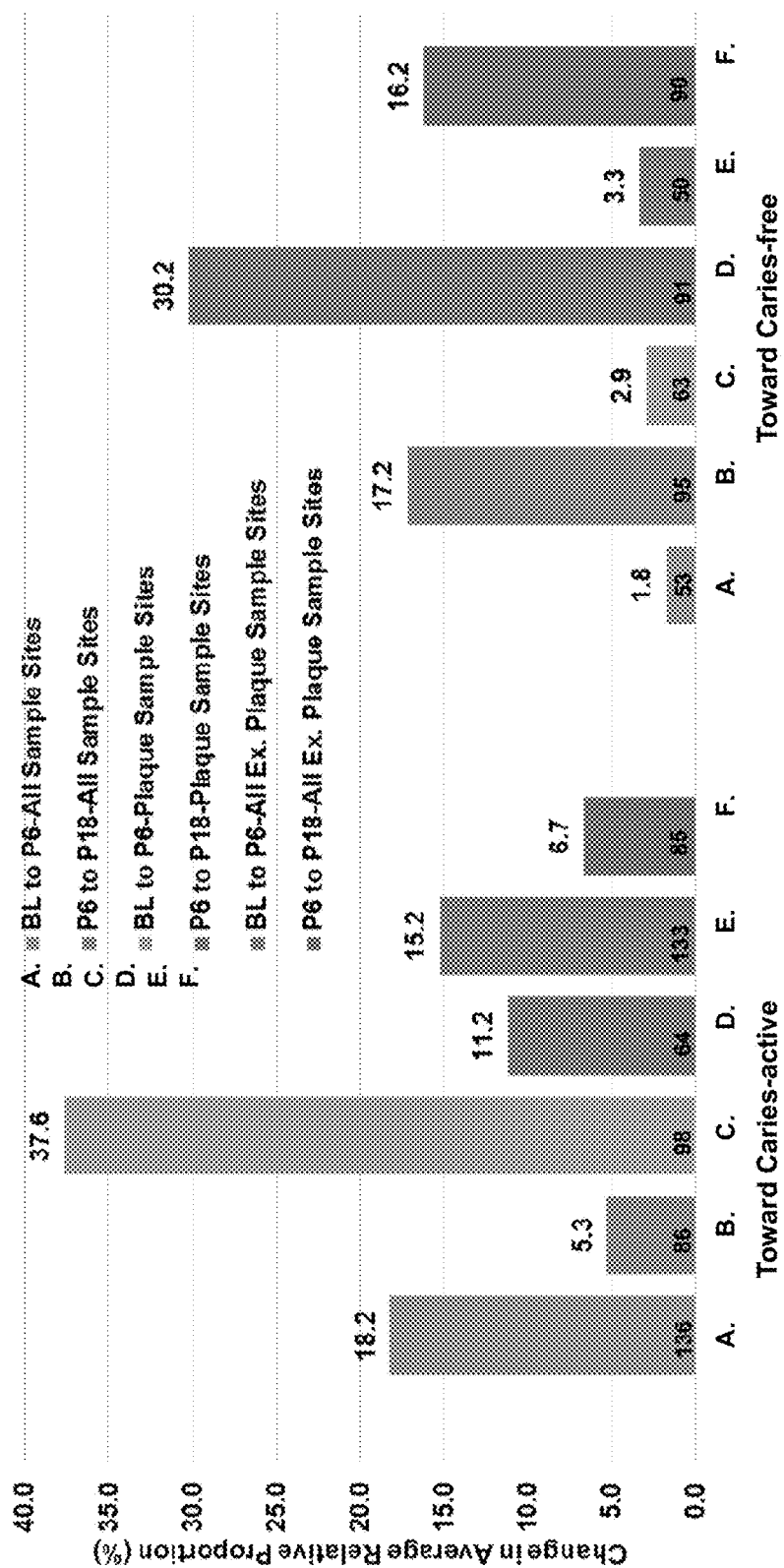
FIG. 6. Change in Average Relative Proportion (%) from Baseline (BL) to P6 and P6 to P18 per HOMINGS for "Caries-free" and "Caries-active" associated species (Tanner et al. 2016), with addition of other known species corresponding to genera of defined species (Tanner et al. 2016). Numbers at bottom of bars represent the number of species detected; *S. sanguinis* was considered "caries-free" associated species; all patients had chemotherapy concurrent to radiation therapy, were antibiotic free for at least 2 weeks prior to sampling, and did not receive induction chemotherapy.
Figure 7:
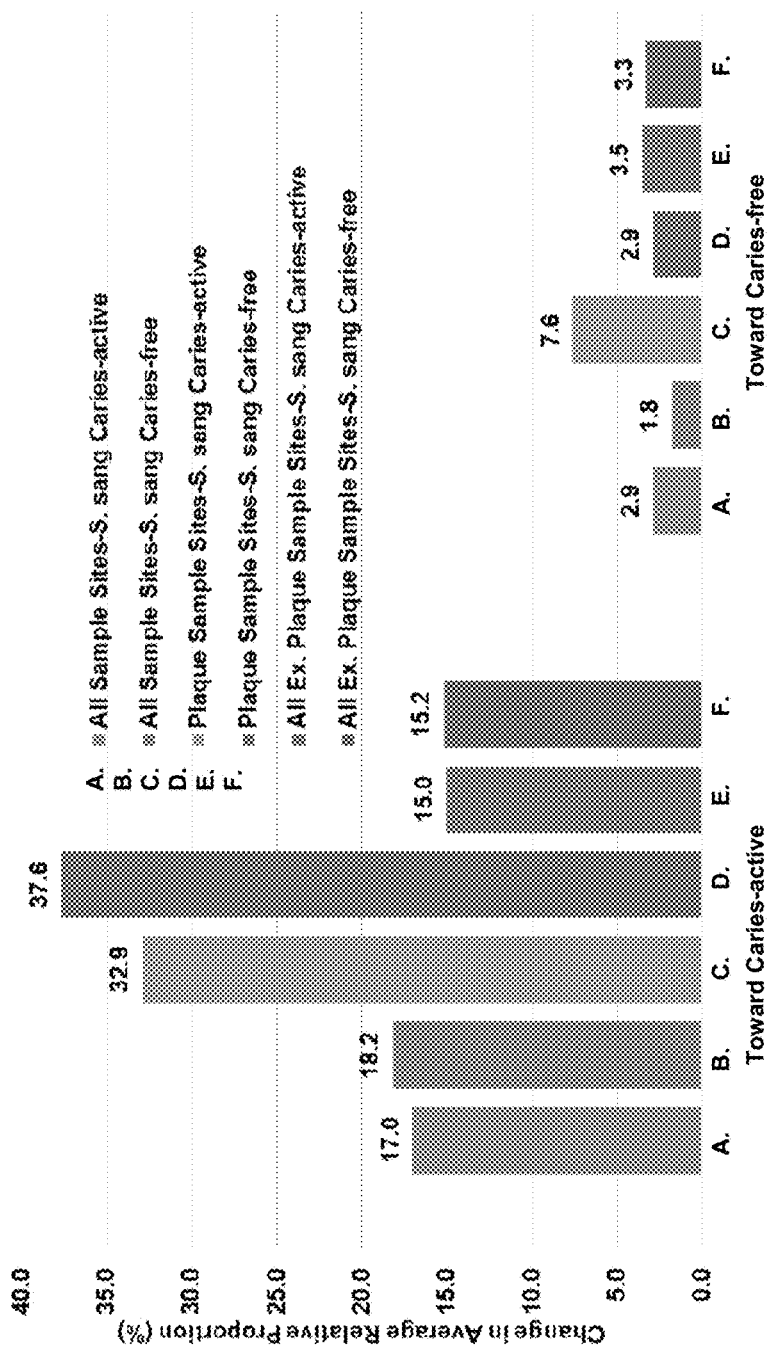
FIG. 7. Change in Average Relative Proportion (%) from Baseline (BL) to P6 and P6 to P18 per HOMINGS for "Caries-free" and "Caries-active" associated species (Tanner et al. 2016), considering *S. sanguinis* either as caries-free or as caries-active associated species. Numbers at bottom of bars represent the number of species detected; all patients had chemotherapy concurrent to radiation therapy, were antibiotic free for at least 2 weeks prior to sampling, and did not receive induction chemotherapy. The literature describes *S. sanguinis* as a health-associated species.

The change in relative proportions described above was further broken down by sample site to determine which sample sites contribute most significantly to the determination of caries health or disease. The same process that was used to assess overall change in relative proportion noted above was applied by sample site, i.e., buccal, plaque, saliva and tongue. We determined that plaque was the strongest contributor to the movement toward disease in all scenarios, as shown in bar graphs (FIGS. 5-7) and results from Wilcoxon signed-rank and McNemar tests p-values (Tables 7 and 8).

Taking the analysis to a final step, the species responsible for the movement toward disease in the plaque samples were identified for the BL to P6 and P6 to P18 scenarios. A total of ten species with greatest relative proportion changes (%), BL to P6 compared to P6 to P18, are shown in tables for the analyses "Species Only" and "Species+Genera" (Tables 9 and 10, respectively). *Streptococcus mutans* was the species representing the greatest change toward disease and the reversal toward health in dental plaque.\

This analysis examines the possibility of a shift towards dysbiosis whereby caries disease-associated species are more predominant than caries-free associated species at P6 and whether the dental health status is likely to return to normality at P18.

Disease-associated species are known to be acidogenic and aciduric, while health associated species may contribute to alkalinization. A good predictor to determine risk (via multiple logistic regression analysis and ROC curves) will require the bacterial abundance data to be accompanied with other measurements. While one cannot allocate a weight value of contribution by each species within the biofilm of dental plaque, pH or cariogenicity measurements in saliva and knowledge of carbohydrate consumption, and level of inflammation/oxidative stress (e.g., C-reactive protein [CRP]/periodontal disease/8-ODG levels in saliva), can be obtained. As a test for cariogenicity and acquisition of carbohydrate consumption, we will use the Cariscreen test (assay+questionnaire; CariFree—National Dental Inc., Canada).

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

| Specifically Named Species |
|---|
| Abiotrophia_defectiva |
| Actinomyces_gerencseriae |
| Actinomyces_israelii |
| Actinomyces_naeslundii |
| Actinomyces_odontolyticus |
| Atopobium_parvulum |
| Bifidobacterium_breve |
| Bifidobacterium_dentium |
| Capnocytophaga_gingivalis |
| Capnocytophaga_granulosa |
| Cardiobacterium_hominis |
| Corynebacterium_durum |
| Corynebacterium_matruchotii |
| Dialister_invisus |
| Enterococcus_faecalis |
| Fusobacterium_nucleatum_subsp_animalis |
| Fusobacterium_nucleatum_subsp_nucleatum |
| Fusobacterium_nucleatum_subsp_polymorphum |
| Fusobacterium_nucleatum_subsp_vincentii |
| Fusobacterium_periodonticum |
| Gemella_haemolysans |
| Granulicatella_elegans |
| Kingella_oralis |
| Lactobacillus_fermentum |
| Lactococcus_lactis |
| Megasphaera_micronuciformis |
| Neisseria_elongata |
| Olsenella_profusa |
| Parascardovia_denticolens |
| Prevotella_denticola |
| Prevotella_melaninogenica |
| Pseudoramibacter_alactolyticus |
| Rothia_dentocariosa |
| Scardovia_inopinata |
| Scardovia_wiggsiae |
| Selenomonas_sputigena |
| Solobacterium_moorei |
| Streptococcus_cristatus |
| Streptococcus_intermedius |
| Streptococcus_mutans |
| Streptococcus_parasanguinis_II |
| Streptococcus_sanguinis |
| Streptococcus_sobrinus |
| Veillonella_dispar |
| Veillonella_parvula |
| Veillonellaceae [G-1]_sp_oral_taxon_155 |
| Veillonella_atypica |

Unbold = Caries-free;
Bold = Caries-active (n = 46)

| Specifically Named Species plus Named Genera |
|---|
| Abiotrophia_defectiva |
| Actinomyces_cardiffensis |
| Actinomyces_georgiae |
| Actinomyces_gerencseriae |
| Actinomyces_graevenitzii |
| Actinomyces_israelii |
| Actinomyces_johnsonii |
| Actinomyces_massiliensis |
| Actinomyces_meyeri |
| Actinomyces_naeslundii |
| Actinomyces_odontolyticus |
| Actinomyces_oricola |
| Actinomyces_radicidentis |
| Actinomyces_sp_oral_taxon_169 |
| Actinomyces_sp_oral_taxon_170 |
| Actinomyces_sp_oral_taxon_171 |
| Actinomyces_sp_oral_taxon_172 |
| Actinomyces_sp_oral_taxon_175 |
| Actinomyces_sp_oral_taxon_178 |
| Actinomyces_sp_oral_taxon_180 |
| Actinomyces_sp_oral_taxon_181 |
| Actinomyces_sp_oral_taxon_414 |
| Actinomyces_sp_oral_taxon_446 |
| Actinomyces_sp_oral_taxon_448 |
| Actinomyces_sp_oral_taxon_525 |
| Actinomyces_sp_oral_taxon_848 |
| Actinomyces_sp_oral_taxon_877 |
| Actinomyces_sp_oral_taxon_896 |
| Actinomyces_sp_oral_taxon_897 |
| Actinomyces_timonensis |
| Actinomyces_viscosus |
| Actinomyces_graevenitzii |
| Actinomyces_naeslundii |
| Actinomyces_odontolyticus |
| Actinomyces_radicidentis |
| Actinomyces_sp_oral_taxon_525 |
| Actinomyces_timonensis |
| Atopobium_minutum |
| Atopobium_parvulum |
| Atopobium_rimae |
| Atopobium_sp_oral_taxon_199 |
| Atopobium_sp_oral_taxon_416 |
| Atopobium_sp_oral_taxon_810 |
| Atopobium_vaginae |
| Bifidobacterium_animalis_subsp_animalis |
| Bifidobacterium_animalis_subsp_lactis |
| Bifidobacterium_breve |
| Prevotella_loescheii |
| Prevotella_maculosa |
| Prevotella_marshii |
| Prevotella_melaninogenica |
| Prevotella_micans |
| Prevotella_multiformis |
| Prevotella_multisaccharivorax |
| Prevotella_nigrescens |
| Prevotella_oralis |
| Prevotella_oris |
| Prevotella_oulorum |
| Prevotella_pallens |
| Prevotella_pleuritidis |
| Prevotella_saccharolytica |
| Prevotella_salivae |
| Prevotella_scopos |
| Prevotella_shahii |
| Prevotella_sp_oral_taxon_292 |
| Prevotella_sp_oral_taxon_293 |
| Prevotella_sp_oral_taxon_296 |
| Prevotella_sp_oral_taxon_300 |

| Specifically Named Species plus Named Genera |
|---|
| Prevotella_sp_oral_taxon_301 |
| Prevotella_sp_oral_taxon_304 |
| Prevotella_sp_oral_taxon_305 |
| Prevotella_sp_oral_taxon_306 |
| Prevotella_sp_oral_taxon_309 |
| Prevotella_sp_oral_taxon_310 |
| Prevotella_sp_oral_taxon_315 |
| Prevotella_sp_oral_taxon_317 |
| Prevotella_sp_oral_taxon_376 |
| Prevotella_sp_oral_taxon_396 |
| Prevotella_sp_oral_taxon_443 |
| Prevotella_sp_oral_taxon_472 |
| Prevotella_sp_oral_taxon_475 |
| Prevotella_sp_oral_taxon_515 |
| Prevotella_sp_oral_taxon_526 |
| Prevotella_sp_oral_taxon_820 |
| Prevotella_veroralis |
| Propionibacterium_acidifaciens |
| Propionibacterium_acnes |
| Propionibacterium_avidum |
| Propionibacterium_propionicum |
| Propionibacterium_sp_oral_taxon_192 |
| Propionibacterium_sp_oral_taxon_193 |
| Propionibacterium_sp_oral_taxon_194 |
| Propionibacterium_sp_oral_taxon_915 |
| Prevotella_enoeca |
| Prevotella_fusca |
| Prevotella_intermedia |
| Prevotella_loescheii |
| Prevotella_marshii |
| Prevotella_micans |
| Veillonella_parvula |
| Veillonella_rogosae |
| Veillonella_sp_oral_taxon_780 |
| Veillonella_sp_oral_taxon_917 |
| Veillonella_denticariosi |
| Veillonellaceae [G-1]_sp_oral_taxon_155 |
| Veillonella_atypica |
| Bifidobacterium_dentium |
| Bifidobacterium_longum |
| Bifidobacterium_scardovi |
| Capnocytophaga_gingivalis |
| Capnocytophaga_granulosa |
| Cardiobacterium_hominis |
| Corynebacterium_durum |
| Corynebacterium_matruchotii |
| Dialister_invisus |
| Enterococcus_faecalis |
| Fusobacterium_nucleatum_subsp_animalis |
| Fusobacterium_nucleatum_subsp_nucleatum |
| Fusobacterium_nucleatum_subsp_polymorphum |
| Fusobacterium_nucleatum_subsp_vincentii |
| Fusobacterium_periodonticum |
| Gemella_haemolysans |
| Granulicatella_elegans |
| Kingella_oralis |
| Lactobacillus_brevis |
| Lactobacillus_coleohominis |
| Lactobacillus_fermentum |
| Lactobacillus_iners |
| Lactobacillus_jensenii |
| Lactobacillus_kisonensis |
| Lactobacillus_parafarraginis |
| Lactobacillus_reuteri |
| Lactobacillus_salivarius |
| Lactobacillus_sp_oral_taxon_052 |
| Lactobacillus_vaginalis |
| Lactococcus_lactis |
| Megasphaera_micronuciformis |
| Neisseria_elongata |

| Specifically Named Species plus Named Genera |
|---|
| *Olsenella_profusa* |
| *Olsenella_sp_oral_taxon_807* |
| *Olsenella_sp_oral_taxon_809* |
| *Olsenella_uli* |
| *Parascardovia_denticolens* |
| *Prevotella_baroniae* |
| *Prevotella_bivia* |
| *Prevotella_buccae* |
| *Prevotella_buccalis* |
| *Prevotella_dentalis* |
| *Prevotella_denticola* |
| *Prevotella_enoeca* |
| *Prevotella_pallens* |
| *Prevotella_fusca* |
| *Prevotella_histicola* |
| *Prevotella_intermedia* |
| *Prevotella_saccharolytica* |
| *Prevotella_sp_oral_taxon_317* |
| *Pseudoramibacter_alactolyticus* |
| *Rothia_dentocariosa* |
| *Scardovia_inopinata* |
| *Scardovia_wiggsiae* |
| *Selenomonas_artemidis* |
| *Selenomonas_dianae* |
| *Selenomonas_flueggei* |
| *Selenomonas_noxia* |
| *Selenomonas_sp_oral_taxon_133* |
| *Selenomonas_sp_oral_taxon_134* |
| *Selenomonas_sp_oral_taxon_136* |
| *Selenomonas_sp_oral_taxon_137* |
| *Selenomonas_sp_oral_taxon_138* |
| *Selenomonas_sp_oral_taxon_143* |
| *Selenomonas_sp_oral_taxon_146* |
| *Selenomonas_sp_oral_taxon_149* |
| *Selenomonas_sp_oral_taxon_388* |
| *Selenomonas_sp_oral_taxon_442* |
| *Selenomonas_sp_oral_taxon_478* |
| *Selenomonas_sp_oral_taxon_501* |
| *Selenomonas_sputigena* |
| *Selenomonas_artemidis* |
| *Selenomonas_dianae* |
| *Selenomonas_sp_oral_taxon_133* |
| *Selenomonas_sp_oral_taxon_134* |
| *Selenomonas_sp_oral_taxon_136* |
| *Selenomonas_sp_oral_taxon_137* |
| *Selenomonas_sp_oral_taxon_478* |
| *Solobacterium_moorei* |
| *Streptococcus_agalactiae* |
| *Streptococcus_anginosus* |
| *Streptococcus_constellatus* |
| Streptococcus_cristatus |
| *Streptococcus_downei* |
| *Streptococcus_intermedius* |
| *Streptococcus_mutans* |
| *Streptococcus_parasanguinis_II* |
| *Streptococcus_pyogenes* |
| Streptococcus_sanguinis |
| *Streptococcus_sobrinus* |
| *Streptococcus_sp_oral_taxon_064* |
| *Streptococcus_sp_oral_taxon_066* |
| *Streptococcus_sp_oral_taxon_068* |
| *Streptococcus_sp_oral_taxon_069* |
| *Streptococcus_sp_oral_taxon_431* |
| *Streptococcus_sp_oral_taxon_486* |
| *Streptococcus_sp_oral_taxon_487* |
| *Veillonella_denticariosi* |
| *Veillonella_dispar* |

Unbold = Caries-free;
Bold = Caries-active (n = 205)

TABLE 1

Numbers of species detected by HOMINGS

| Site: Patient | Mean | Std. Dev. | Minimum | Maximum |
|---|---|---|---|---|
| Plaque: HC | 120 | 42 | 44 | 186 |
| SCC | 92 | 31 | 60 | 165 |
| SCC + Chemo | 138 | 46 | 61 | 215 |
| Total | 115 | 42 | 44 | 215 |
| Saliva: HC | 153 | 32 | 82 | 205 |
| SCC | 124 | 25 | 75 | 171 |
| SCC + Chemo | 159 | 52 | 73 | 250 |
| Total | 144 | 38 | 73 | 250 |
| Combined | 130 | 42 | 44 | 250 |

TABLE 2

Alpha diversity analysis HC vs. SCC vs. SCC + chemo groups

| Source | DF | Sum of squares | Mean squares | F | Pr > F |
|---|---|---|---|---|---|
| Simpson-Analysis of variance: | | | | | |
| Model | 5 | 0.227 | 0.045 | 5.356 | 0.000 |
| Error | 72 | 0.610 | 0.008 | | |
| Corrected Total | 77 | 0.838 | | | |
| Shannon-Analysis of variance: | | | | | |
| Model | 5 | 4.977 | 0.995 | 4.096 | 0.002 |
| Error | 72 | 17.498 | 0.243 | | |
| Corrected Total | 77 | 22.476 | | | |

Computed against model Y = Mean(Y)

| Contrast | Difference | Standardized difference | Critical value | Pr > Diff | Significant |
|---|---|---|---|---|---|
| Simpson-Diagnosis/Tukey (HSD)/Analysis of the differences between the categories Confidence Interval 95% | | | | | |
| SCC vs. SCC + CH | −0.097 | −3.420 | 2.393 | 0.003 | Yes |
| SCC vs. HC | −0.070 | −2.919 | 2.393 | 0.013 | Yes |
| HC vs. SCC + CH | −0.027 | −0.989 | 2.393 | 0.586 | No |
| Tukey's d critical value: | | | 3.385 | | |
| Shannon- Diagnosis/Tukey (HSD)/Analysis of the differences between the categories Confidence Interval 95% | | | | | |
| SCC vs. SCC + CH | −0.511 | −3.383 | 2.393 | 0.003 | Yes |
| SCC vs. HC | −0.381 | −2.965 | 2.393 | 0.011 | Yes |
| HC vs. SCC + CH | −0.131 | −0.909 | 2.393 | 0.636 | No |
| Tukey's d critical value: | | | 3.385 | | |

TABLE 3

Permutational MANOVA (PERMANOVA) comparing "saliva" vs. "plaque" and HC vs. SCC vs. SCC + chemo groups

PERMANOVA

Permutational MANOVA
Resemblance worksheet

Name: Resem1
Data type: Similarity
Selection: All
Transform: Square root
Resemblance: S17 Bray Curtis similarity
Covariables worksheet Name: Data1
Data type: Environmental
Sample selection: All
Variable selection: All
Sums of squares type: Type I (sequential)
Fixed effects sum to zero for mixed terms Permutation method: Permutation of residuals under a reduced model
Number of permutations: 9999

Factors

| Name | Abbrev. | Type | Levels |
|---|---|---|---|
| Diagnosis | Di | Fixed | 3 |
| Site | Si | Fixed | 2 |

Contrasts

| Name | Abbrev. | Factor | Contrast |
|---|---|---|---|
| C1 | C1 | Diagnosis | (Healthy)v(SCC) |
| C2 | C2 | Diagnosis | (Healthy)v(SCC&Chem) |
| C3 | C3 | Diagnosis | (SCC)v(SCC&Chem) |

PERMANOVA table of results

| Source | df | SS | MS | Pseudo-F | P (perm) | Unique perms | P (MC) |
|---|---|---|---|---|---|---|---|
| Pac | 1 | 2978.9 | 2978.9 | 1.702 | 0.0364 | 9900 | 0.0371 |
| Pas | 1 | 2374.4 | 2374.4 | 1.3566 | 0.1061 | 9885 | 0.1337 |

TABLE 3-continued

Permutational MANOVA (PERMANOVA) comparing "saliva" vs. "plaque" and HC vs. SCC vs. SCC + chemo groups

| | | | | | | | | |
|---|---|---|---|---|---|---|---|---|
| Cu | 1 | 2793.7 | 2793.7 | 1.5962 | 0.0492 | 9883 | 0.0539 | |
| Di | 2 | 12790 | 6395.1 | 3.6539 | 0.0001 | 9882 | 0.0001 | Diagnosis |
| C1 | 1 | 3601.4 | 3601.4 | 2.0796 | 0.0056 | 9892 | 0.0103 | p-values |
| C2 | 1 | 8607.9 | 8607.9 | 5.1036 | 0.0001 | 9919 | 0.0002 | |
| C3 | 1 | 8019.6 | 8019.6 | 4.4172 | 0.0001 | 9912 | 0.0002 | |
| Si | 1 | 19594 | 19594 | 11.195 | 0.0001 | 9900 | 0.0001 | Site p-value |
| Di × Si | 2 | 2858.9 | 1429.4 | 0.81672 | 0.8306 | 9847 | 0.7795 | |
| C1 × Si | 1 | 1466.3 | 1466.3 | 0.84671 | 0.6781 | 9905 | 0.6349 | Diagnosis × Site |
| C2 × Si | 1 | 1438.8 | 1438.8 | 0.85307 | 0.652 | 9894 | 0.6019 | Interactions |
| C3 × Si | 1 | 1368 | 1368 | 0.75351 | 0.7984 | 9903 | 0.7233 | p-values |
| Res | 69 | 1.2076E5 | 1750.2 | | | | | |
| Total | 77 | 1.6415E5 | | | | | | |

TABLE 4

SIMPER analysis

| Species | Group SCC Av. Abund | Group SCC&Chem Av. Abund | Av. Diss | Diss/SD | Contrib % | Cum. % |
|---|---|---|---|---|---|---|
| PR-1 | 25.96 | 30.94 | 1.91 | 1.03 | 2.83 | 12.44 |
| PR-2 | 9.54 | 17.30 | 0.85 | 1.14 | 1.26 | 26.89 |
| PR-3 | 8.91 | 11.13 | 0.85 | 0.84 | 1.25 | 28.15 |
| PR-4 | 2.88 | 12.35 | 0.62 | 1.20 | 0.91 | 40.66 |
| PR-5 | 4.15 | 10.89 | 0.58 | 1.13 | 0.86 | 43.29 |
| PR-6 | 3.23 | 10.94 | 0.58 | 1.19 | 0.85 | 45.00 |

Groups SCC & SCC&Chem
Average dissimilarity = 67.67

TABLE 5

Numbers of species detected by HOMINGS

| | | Pre-RT Number of Species | | | | Post-RT Number of Species | | | |
|---|---|---|---|---|---|---|---|---|---|
| | | Mean | Std Dev | Min | Max | Mean | Std Dev | Min | Max |
| Patients | Mucosa n = 8 | 99 | 26 | 63 | 144 | 105 | 30 | 52 | 135 |
| | Plaque n = 8 | 129 | 51 | 61 | 228 | 114 | 51 | 40 | 212 |
| | Tongue n = 8 | 102 | 39 | 61 | 182 | 100 | 32 | 41 | 139 |
| Overall | | 110 | 41 | 61 | 228 | 106 | 38 | 40 | 212 |

TABLE 6

| Species | | Pre Av. Abund | Post Av. Abund | Fold-Change | Av. Diss | Diss/SD | Contrib % |
|---|---|---|---|---|---|---|---|
| Abiotrophia defectiva | AB-01 | 4.73 | 2.36 | 0.498942918 | 0.37 | 0.47 | 0.53 |
| Actinomyces gerencseriae | AC-07 | 0.19 | 1.98 | 10.42105263 | 0.12 | 0.52 | 0.18 |
| Actinomyces israelii | AC-09 | 2.43 | 1.79 | 0.736625514 | 0.18 | 0.74 | 0.26 |
| Actinomyces meyeri | AC-12 | 0.46 | 1.77 | 3.847826087 | 0.12 | 0.76 | 0.17 |
| Actinomyces naeslundii | AC-36 | 0.54 | 5.01 | 9.277777778 | 0.32 | 0.95 | 0.46 |
| Actinomyces odontolyticus | AC-37 | 0.55 | 3.98 | 7.236363636 | 0.29 | 0.6 | 0.42 |
| Actinomyces odontolyticus | AC-14 | 0.83 | 1.48 | 1.78313253 | 0.13 | 0.56 | 0.19 |
| Alloprevotella tannerae | AL-09 | 3.9 | 2.62 | 0.671794872 | 0.29 | 0.94 | 0.41 |
| Atopobium parvulum | AT-08 | 1.2 | 1.45 | 1.208333333 | 0.12 | 0.82 | 0.17 |
| Atopobium parvulum | AT-02 | 8.09 | 9.64 | 1.191594561 | 0.68 | 1.1 | 0.98 |
| Atopobium rimae | AT-03 | 6.16 | 8.33 | 1.352272727 | 0.6 | 0.91 | 0.87 |
| Bacteroidaceae [G1] sp oral taxon 272 | BA-02 | 1.13 | 2.22 | 1.96460177 | 0.18 | 0.58 | 0.26 |
| Bacteroidales [G2] sp oral taxon 274 | BA-03 | 1.72 | 2.4 | 1.395348837 | 0.18 | 0.96 | 0.26 |
| Bifidobacterium dentium | BI-05 | 1.41 | 3.87 | 2.744680851 | 0.26 | 0.71 | 0.37 |

TABLE 6-continued

| | | | | | | | |
|---|---|---|---|---|---|---|---|
| *Bifidobacterium longum* | BI-06 | 1.04 | 0.72 | 0.692307692 | 0.1 | 0.64 | 0.14 |
| *Campylobacter concisus* | CA-02 | 8.74 | 9.22 | 1.054919908 | 0.85 | 0.66 | 1.22 |
| *Campylobacter concisus* | CA-01 | 4.85 | 1.6 | 0.329896907 | 0.3 | 0.86 | 0.43 |
| *Campylobacter curvus* | CA-03 | 2.12 | 0.98 | 0.462264151 | 0.14 | 0.63 | 0.2 |
| *Campylobacter gracilis* | CA-04 | 11.11 | 17 | 1.530153015 | 1.04 | 1.24 | 1.5 |
| *Capnocytophaga gingivalis* | CA-09 | 8.24 | 5.39 | 0.654126214 | 0.52 | 1.18 | 0.75 |
| *Capnocytophaga sputigena* | CA-30 | 1.56 | 1.83 | 1.173076923 | 0.17 | 0.65 | 0.25 |
| *Cardiobacterium hominis* | CA-31 | 2.31 | 1 | 0.432900433 | 0.16 | 0.61 | 0.24 |
| *Corynebacterium matruchotii* | CO-03 | 6.79 | 3.26 | 0.48011782 | 0.4 | 0.81 | 0.57 |
| *Cryptobacterium curtum* | CR-01 | 0.61 | 2.02 | 3.31147541 | 0.14 | 0.72 | 0.2 |
| *Desulfobulbus* sp oral taxon 041 | DE-02 | 1.29 | 2.13 | 1.651162791 | 0.2 | 0.43 | 0.28 |
| *Dialister invisus* | DI-01 | 3.51 | 14.01 | 3.991452991 | 0.82 | 1.03 | 1.17 |
| *Dialister pneumosintes* | DI-03 | 1.28 | 3.03 | 2.3671875 | 0.21 | 0.77 | 0.31 |
| *Eikenella corrodens* | EI-01 | 3.06 | 2.38 | 0.777777778 | 0.25 | 0.85 | 0.36 |
| *Enterococcus faecalis* | EN-02 | 0.51 | 17.1 | 33.52941176 | 1.15 | 0.23 | 1.65 |
| *Eubacterium* [11][G-1] *infirmum* | EU-02 | 2.05 | 1.54 | 0.751219512 | 0.15 | 0.98 | 0.22 |
| *Eubacterium* [11][G-3] brachy | EU-04 | 1.91 | 6 | 3.141361257 | 0.36 | 0.86 | 0.52 |
| *Eubacterium* [11][G-5] *saphenum* | EU-05 | 0.79 | 1.09 | 1.379746835 | 0.12 | 0.49 | 0.17 |
| *Fretibacterium fastidiosum* | FR-01 | 3.95 | 3.83 | 0.969620253 | 0.32 | 1.02 | 0.46 |
| *Fretibacterium* sp oral taxon 360 | FR-04 | 0.96 | 1.81 | 1.885416667 | 0.15 | 0.45 | 0.21 |
| *Fusobacterium nucleatum* subsp *animalis* | FU-05 | 0.81 | 1.44 | 1.777777778 | 0.09 | 0.92 | 0.14 |
| *Fusobacterium nucleatum* subsp *nucleatum* | FU-07 | 1.5 | 3.03 | 2.02 | 0.16 | 0.86 | 0.23 |
| *Fusobacterium nucleatum* subsp *polymorphum* | FU-08 | 0.66 | 1.56 | 2.363636364 | 0.1 | 1.1 | 0.14 |
| *Fusobacterium nucleatum* subsp *vincentii* | FU-09 | 0.76 | 2.26 | 2.973684211 | 0.13 | 1.27 | 0.19 |
| *Fusobacterium periodonticum* | FU-10 | 10.32 | 4.73 | 0.458333333 | 0.63 | 0.64 | 0.91 |
| *Gemella haemolysans* | GE-02 | 47.85 | 28.35 | 0.592476489 | 2.73 | 1.08 | 3.93 |
| *Gemella morbillorum* | GE-03 | 4.52 | 4.56 | 1.008849558 | 0.36 | 0.94 | 0.52 |
| *Gemella morbillorum* | GE-05 | 3.26 | 1.76 | 0.539877301 | 0.23 | 0.83 | 0.33 |
| *Granulicatella elegans* | GR-02 | 14.24 | 1.29 | 0.090589888 | 0.95 | 0.57 | 1.37 |
| *Haemophilus parainfluenzae* | HA-05 | 10.85 | 8.01 | 0.738248848 | 0.8 | 0.82 | 1.15 |
| *Lachnoanaerobaculum saburreum* | LA-02 | 4.66 | 3.67 | 0.787553648 | 0.33 | 1.08 | 0.48 |
| Lachnospiraceae [G2] sp oral taxon 096 | LA-08 | 0.5 | 2.32 | 4.64 | 0.15 | 0.37 | 0.22 |
| Lachnospiraceae [G7] sp oral taxon 086 | LA-13 | 0.37 | 2.27 | 6.135135135 | 0.15 | 0.87 | 0.22 |
| *Lactobacillus fermentum* | LA-18 | 0.86 | 5.72 | 6.651162791 | 0.49 | 0.49 | 0.71 |
| *Lactobacillus salivarius* | LA-25 | 2.72 | 0.79 | 0.290441176 | 0.23 | 0.39 | 0.33 |
| *Lactococcus lactis* | LA-28 | 1.17 | 6.84 | 5.846153846 | 0.53 | 0.33 | 0.76 |
| *Lautropia mirabilis* | LA-29 | 5.7 | 2.42 | 0.424561404 | 0.38 | 0.73 | 0.54 |
| *Leptotrichia wadei* | LE-22 | 16.53 | 4.58 | 0.27707199 | 0.98 | 0.89 | 1.4 |
| *Megasphaera micronuciformis* | ME-01 | 0.82 | 2.93 | 3.573170732 | 0.19 | 0.71 | 0.27 |
| *Mogibacterium timidum* | MO-04 | 1.47 | 2 | 1.360544218 | 0.17 | 0.73 | 0.24 |
| *Neisseria bacilliformis* | NE-01 | 1.8 | 0.26 | 0.144444444 | 0.11 | 0.8 | 0.16 |
| *Neisseria elongata* | NE-02 | 1.37 | 1.03 | 0.751824818 | 0.11 | 0.43 | 0.16 |
| *Neisseria flavescens* | NE-03 | 1.73 | 1.56 | 0.901734104 | 0.15 | 0.76 | 0.22 |
| *Parascardovia denticolens* | PA-02 | 0.3 | 2.62 | 8.733333333 | 0.16 | 0.94 | 0.23 |
| *Parvimonas micra* | PA-03 | 5.21 | 9.42 | 1.80806142 | 0.58 | 0.8 | 0.84 |
| *Porphyromonas endodontalis* | PO-03 | 2.78 | 4.18 | 1.503597122 | 0.33 | 0.83 | 0.47 |

TABLE 6-continued

| | | | | | | | |
|---|---|---|---|---|---|---|---|
| *Porphyromonas gingivalis* | PO-05 | 0.81 | 0.82 | 1.012345679 | 0.09 | 0.61 | 0.13 |
| *Prevotella denticola* | PR-06 | 5.35 | 4.36 | 0.814953271 | 0.36 | 1.05 | 0.51 |
| *Prevotella melaninogenica* | PR-14 | 16.51 | 11.92 | 0.721986675 | 1.33 | 0.58 | 1.92 |
| *Prevotella nigrescens* | PR-18 | 2.71 | 4.41 | 1.627306273 | 0.28 | 1.01 | 0.41 |
| *Prevotella oralis* | PR-19 | 0.8 | 2.12 | 2.65 | 0.14 | 0.76 | 0.21 |
| *Prevotella oris* | PR-20 | 4.42 | 8.4 | 1.900452489 | 0.48 | 1.04 | 0.69 |
| *Prevotella pallens* | PR-70 | 0.49 | 2.49 | 5.081632653 | 0.16 | 0.4 | 0.24 |
| *Prevotella veroralis* | PR-51 | 1.63 | 3.78 | 2.319018405 | 0.28 | 0.39 | 0.41 |
| *Pseudoramibacter alactolyticus* | PS-06 | 0.54 | 2.32 | 4.296296296 | 0.17 | 0.63 | 0.24 |
| *Rothia dentocariosa* | RO-02 | 22.96 | 51.28 | 2.233449477 | 2.98 | 1.17 | 4.28 |
| *Scardovia wiggsiae* | SC-02 | 2.48 | 10.94 | 4.411290323 | 0.79 | 0.4 | 1.14 |
| *Selenomonas noxia* | SE-05 | 4.24 | 7.29 | 1.719339623 | 0.54 | 1.02 | 0.78 |
| *Selenomonas noxia* | SE-04 | 5.22 | 1.69 | 0.323754789 | 0.34 | 0.78 | 0.49 |
| *Selenomonas sputigena* | SE-32 | 0.56 | 1.42 | 2.535714286 | 0.1 | 0.68 | 0.15 |
| *Selenomonas sputigena* | SE-18 | 1.34 | 1.56 | 1.164179104 | 0.12 | 1.01 | 0.18 |
| *Selenomonas sputigena* | SE-19 | 1.21 | 0.76 | 0.628099174 | 0.1 | 0.76 | 0.14 |
| *Shuttleworthia satelles* | SH-01 | 0.48 | 2.64 | 5.5 | 0.17 | 0.83 | 0.25 |
| *Solobacterium moorei* | SO-01 | 3.21 | 4.66 | 1.451713396 | 0.28 | 1.17 | 0.4 |
| *Streptococcus anginosus* | ST-09 | 4 | 10.31 | 2.5775 | 0.65 | 0.58 | 0.94 |
| *Streptococcus constellatus* | ST-10 | 6.02 | 9.41 | 1.563122924 | 0.68 | 0.93 | 0.98 |
| *Streptococcus intermedius* | ST-14 | 4.01 | 7.87 | 1.962593516 | 0.46 | 1.38 | 0.66 |
| *Streptococcus mutans* | ST-15 | 18.88 | 18.73 | 0.992055085 | 1.49 | 0.98 | 2.15 |
| *Streptococcus parasanguinis* II | ST-16 | 6.11 | 4.79 | 0.78396072 | 0.2 | 1.2 | 0.29 |
| *Streptococcus sanguinis* | ST-20 | 16.4 | 9.16 | 0.558536585 | 0.8 | 1.05 | 1.14 |
| *Tannerella forsythia* | TA-01 | 1.79 | 3.79 | 2.117318436 | 0.29 | 0.47 | 0.42 |
| *Veillonella atypica* | VE-20 | 7 | 6.53 | 0.932857143 | 0.64 | 0.8 | 0.91 |
| *Veillonella atypica* | VE-21 | 7.04 | 5.9 | 0.838068182 | 0.59 | 0.81 | 0.85 |
| *Veillonella denticariosi* | VE-02 | 2.13 | 3.1 | 1.455399061 | 0.27 | 0.6 | 0.39 |
| *Veillonella dispar* | VE-03 | 22.25 | 18.13 | 0.814831461 | 1.28 | 0.95 | 1.83 |
| *Veillonella parvula* | VE-06 | 3.95 | 8.9 | 2.253164557 | 0.6 | 0.87 | 0.86 |
| *Veillonella parvula* | VE-05 | 2.43 | 0.41 | 0.16872428 | 0.17 | 0.56 | 0.24 |
| Veillonellaceae [G1] sp oral taxon 155 | VE-15 | 1.92 | 2.2 | 1.145833333 | 0.17 | 1.15 | 0.25 |

| | Species | Cum. % | Caries | Perio-dontits | Comments | PMID |
|---|---|---|---|---|---|---|
| *Abiotrophia defectiva* | AB-01 | 58.88 | negative | | negatively associated with caries | PMC120252 |
| *Actinomyces gerencseriae* | AC-07 | 85.7 | y | y | acidogenic | PMC120252, (2) |
| *Actinomyces israelii* | AC-09 | 76.99 | y | y | | PMC3122858, 26324012, (2) |
| *Actinomyces meyeri* | AC-12 | 86.56 | | y | | 26324012 |
| *Actinomyces naeslundii* | AC-36 | 63.81 | y | y | acidogenic | PMC120253 |
| *Actinomyces odontolyticus* | AC-37 | 65.95 | y | y | | 26324012 |
| *Actinomyces odontolyticus* | AC-14 | 84.59 | y | y | | 26324012 |
| *Alloprevotella tannerae* | AL-09 | 66.78 | y | | | PMC3968045 |
| *Atopobium parvulum* | AT-08 | 86.05 | y | | negative | BRONJ | PMC4447273, 25105817, 12709498 |
| *Atopobium parvulum* | AT-02 | 37.3 | y | | negative | BRONJ | PMC4447273, 25105817, 12709498 |
| *Atopobium rimae* | AT-03 | 43.73 | | | negative | | 12709498 |
| Bacteroidaceae [G1] sp oral taxon 272 | BA-02 | 76.73 | | y | | PMC3627366 |
| Bacteroidales [G2] sp oral taxon 274 | BA-03 | 77.25 | negative | y | | PMC4319720, 26936213, PMC3627366 |
| *Bifidobacterium dentium* | BI-05 | 69.94 | y | y | BRONJ | PMC4319720, 25105817 |
| *Bifidobacterium longum* | BI-06 | 88.27 | y | | | PMC4317471 |

TABLE 6-continued

| | | | | | | |
|---|---|---|---|---|---|---|
| *Campylobacter concisus* | CA-02 | 29.75 | | y | | |
| *Campylobacter concisus* | CA-01 | 64.7 | | y | | |
| *Campylobacter curvus* | CA-03 | 83 | | y | | |
| *Campylobacter gracilis* | CA-04 | 24.51 | y | y | | 19722792 |
| *Capnocytophaga gingivalis* | CA-09 | 50.2 | y | y | | |
| *Capnocytophaga sputigena* | CA-30 | 78 | negative | y | negatively associated with caries | PMC120252 |
| *Cardiobacterium hominis* | CA-31 | 80.17 | | y | | |
| *Corynebacterium matruchotii* | CO-03 | 57.27 | | y | | |
| *Cryptobacterium curtum* | CR-01 | 83.2 | y | y | | PMC4319720, 24504329, 12709498 |
| *Desulfobulbus* sp oral taxon 041 | DE-02 | 74.83 | | y | | 26936213 |
| *Dialister invisus* | DI-01 | 30.92 | y | y | | 26187422, 19722792 |
| *Dialister pneumosintes* | DI-03 | 73.97 | | y | | 12374926 |
| *Eikenella corrodens* | EI-01 | 71.01 | y | y | | 19722792 |
| *Enterococcus faecalis* | EN-02 | 19.92 | y | y | | 17897617, 25048049, PMC3912758 |
| *Eubacterium* [11][G-1] *infirmum* | EU-02 | 81.08 | | y | BRONJ | 25105817, PMC3627366 |
| *Eubacterium* [11][G-3] brachy | EU-04 | 59.93 | | y | | |
| *Eubacterium* [11][G-5] *saphenum* | EU-05 | 86.73 | | y | | 12709498 |
| *Fretibacterium fastidiosum* | FR-01 | 64.27 | | y | | 26936213 |
| *Fretibacterium* sp oral taxon 360 | FR-04 | 81.95 | | y | | 26936213 |
| *Fusobacterium nucleatum* subsp *animalis* | FU-05 | 89.51 | y? | | | |
| *Fusobacterium nucleatum* subsp *nucleatum* | FU-07 | 80.4 | y? | y | | 10816455 |
| *Fusobacterium nucleatum* subsp *polymorphum* | FU-08 | 88.55 | negative | y | negatively associated with caries | PMC120252 |
| *Fusobacterium nucleatum* subsp *vincentii* | FU-09 | 84.78 | y? | y | | |
| *Fusobacterium periodonticum* | FU-10 | 41.97 | y? | y | | |
| *Gemella haemolysans* | GE-02 | 12.37 | negative | y | | 22458262 |
| *Gemella morbillorum* | GE-03 | 60.44 | | y | | |
| *Gemella morbillorum* | GE-05 | 73.34 | | y | | |
| *Granulicatella elegans* | GR-02 | 27.29 | negative/Y | | | 22458262/ PMC3420397 |
| *Haemophilus parainfluenzae* | HA-05 | 32.07 | | y | | |
| *Lachnoanaerobaculum saburreum* | LA-02 | 62.41 | | y | | 18436031 |
| Lachnospiraceae [G2] sp oral taxon 096 | LA-08 | 81.52 | Genus | | | PMC4346134 |
| Lachnospiraceae [G7] sp oral taxon 086 | LA-13 | 81.74 | Genus | | BRONJ | PMC4346134, 25105817 |
| *Lactobacillus fermentum* | LA-18 | 52.38 | y | | Also known to reduce caries | PMC120252 |
| *Lactobacillus salivarius* | LA-25 | 72.36 | y | negative | negatively associated with perio | PMC4405395, 18727656 |
| *Lactococcus lactis* | LA-28 | 49.46 | y | | | |
| *Lautropia mirabilis* | LA-29 | 58.35 | negative | negative | | PMC3592792, PMC3446830 |
| *Leptotrichia wadei* | LE-22 | 25.92 | negative | | | PMC3122858 |
| *Megasphaera micronuciformis* | ME-01 | 75.94 | | y | | PMC4390560 |
| *Mogibacterium timidum* | MO-04 | 78.98 | | y | | 19722792 |

TABLE 6-continued

| | | | | | |
|---|---|---|---|---|---|
| *Neisseria bacilliformis* | NE-01 | 86.89 | negative | | PMC4718657 |
| *Neisseria elongata* | NE-02 | 87.37 | negative | | PMC4718658 |
| *Neisseria flavescens* | NE-03 | 81.3 | negative | | PMC4718659 |
| *Parascardovia denticolens* | PA-02 | 80.64 | y | | PMC4317471, PMC3122858 |
| *Parvimonas micra* | PA-03 | 46.28 | y | y | 26187422, 19722792 |
| *Porphyromonas endodontalis* | PO-03 | 62.88 | y | y | 12709498 |
| *Porphyromonas gingivalis* | PO-05 | 90.04 | y | y | 18287326 |
| *Prevotella denticola* | PR-06 | 60.96 | | y | BRONJ | 25105817, 12709498 |
| *Prevotella melaninogenica* | PR-14 | 16.43 | y | y | | PMC3188461 |
| *Prevotella nigrescens* | PR-18 | 67.19 | y | y | | |
| *Prevotella oralis* | PR-19 | 82.8 | | y | | |
| *Prevotella oris* | PR-20 | 53.07 | | y | | |
| *Prevotella pallens* | PR-70 | 79.93 | | y | | |
| *Prevotella veroralis* | PR-51 | 67.59 | | y | | |
| *Pseudoramibacter alactolyticus* | PS-06 | 79.22 | y | y | | PMC3627366, PMC3077003 |
| *Rothia dentocariosa* | RO-02 | 4.28 | y/ negative | y | | (1), 22739571/ 22458262 |
| *Scardovia wiggsiae* | SC-02 | 34.35 | y | | | PMC3122858 |
| *Selenomonas noxia* | SE-05 | 48.7 | y | y | | PMC4321760, 19722792 |
| *Selenomonas noxia* | SE-04 | 61.44 | y | y | | PMC4321760, 19722793 |
| *Selenomonas sputigena* | SE-32 | 88.12 | y | y | BRONJ | 25105817, 26936213 |
| *Selenomonas sputigena* | SE-18 | 85.87 | y | y | BRONJ | 25105817, 26936213 |
| *Selenomonas sputigena* | SE-19 | 88.69 | y | y | BRONJ | 25105817, 26936213 |
| *Shuttleworthia satelles* | SH-01 | 77.5 | y | y | | PMC4319720, 19722792 |
| *Solobacterium moorei* | SO-01 | 68.4 | negative | y | | PMC3592792, 19722792 |
| *Streptococcus anginosus* | ST-09 | 39.21 | y | y | | 1 |
| *Streptococcus constellatus* | ST-10 | 36.33 | y | y | BRONJ | PMC120252, 25105817, 9495612 |
| *Streptococcus intermedius* | ST-14 | 53.73 | negative | y | | PMC3122858, PMC4410737 |
| *Streptococcus mutans* | ST-15 | 14.52 | y | y | | 8163737, PMC4410737 |
| *Streptococcus parasanguinis* II | ST-16 | 74.55 | negative | y | negatively associated with caries | PMC120252, PMC3754677 |
| *Streptococcus sanguinis* | ST-20 | 33.21 | negative | | negatively associated with caries | PMC120252 |
| *Tannerella forsythia* | TA-01 | 65.12 | | y | | 18287326 |
| *Veillonella atypica* | VE-20 | 41.06 | y | y | | PMC3472979, 19722792 |
| *Veillonella atypica* | VE-21 | 45.44 | y | y | | PMC3472979, 19722792 |
| *Veillonella denticariosi* | VE-02 | 68.79 | y | | | 18296614 |
| *Veillonella dispar* | VE-03 | 18.27 | y | negative | | PMC4317471, PMC3188461 |
| *Veillonella parvula* | VE-06 | 44.59 | y | y | | PMC3122858, PMC4390560 |
| *Veillonella parvula* | VE-05 | 79.7 | y | y | | PMC3122858, PMC4390560 |
| *Veillonellaceae* [G1] sp oral taxon 155 | VE-15 | 77.75 | y | | | PMC3420397 |

SIMPER ANALYSIS
Groups Pre and Post-cancer therapy
Average dissimilarity = 69.56

TABLE 7

Wilcoxon Signed-Rank and McNemar Tests p-values: All Oral Sites Sampled

|  | Species Only | | Species + Genera | |
|---|---|---|---|---|
|  | BL to P6 | P6 to P18 | BL to P6 | P6 to P18 |
| Number of Patients-count | n = 13 | n = 10 | n = 13 | n = 10 |
| Number of Samples-count | n = 43 | n = 28 | n = 43 | n = 28 |
| Species Detected-All Sample Sites-count* | n = 53 | n = 51 | n = 189 | n = 181 |
| Wilcoxon signed-rank test-p-value | 0.0010 | 0.0034 | 0.0006 | 0.0046 |
| McNemar test-Endpoint-p-value | 0.0002 | 0.0270 | 0.0013 | 0.2207 |
| McNemar test-Directional-p-value | 0.0140 | <0.0001 | 0.1096 | <0.0001 |

|  | Species Only-Relative Proportions | | | | | | Species + Genera-Relative Proportions | | | | | |
|---|---|---|---|---|---|---|---|---|---|---|---|---|
|  | Baseline to Post6 | | | Post6 to Post18 | | | Baseline to Post6 | | | Post6 to Post18 | | |
| All Inclusive: | Baseline | Post6 | FC* | Post6 | Post18 | FC* | Baseline | Post6 | FC* | Post6 | Post18 | FC* |
| Mean: Disease (Health) | 0.0087 | 0.1489 | 17.115 | 0.1749 | 0.0933 | −0.533 | 0.0494 | 0.2140 | 4.332 | 0.2696 | 0.1507 | −0.559 |
| Std Dev | 0.1231 | 0.2234 |  | 0.1724 | 0.2081 |  | 0.1541 | 0.2386 |  | 0.1946 | 0.2216 |  |
| Median | −0.0194 | 0.1168 |  | 0.1607 | 0.0294 |  | 0.0069 | 0.2005 |  | 0.2817 | 0.1075 |  |

*FC is fold change in Average Relative Proportion (%) from Baseline to P6 and P6 to P18 per HOMINGS for "Caries-free" and "Caries-active" associated species as defined by Tanner ACR et al., 2016 ("Species Only"), or with the addition of other known species corresponding to genera of species defined by Tanner et al., 2016 ("Species + Genera"). A positive or negative value corresponds to a change toward disease or health respectively. p-values have not been corrected for false discovery.

TABLE 8

Wilcoxon Signed-Rank and McNemar Tests p-values: Plaque Sample Sites Only

|  | Species Only | | Species + Genera | |
|---|---|---|---|---|
|  | BL to P6 | P6 to P18 | BL to P6 | P6 to P18 |
| Number of Patients-count | n = 9 | n = 7 | n = 9 | n = 7 |
| Number of Samples-count | n = 9 | n = 7 | n = 9 | n = 7 |
| Species Detected-All Sample Sites-count* | n = 50 | n = 50 | n = 161 | n = 155 |
| Wilcoxon signed-rank test-p-value | 0.0440 | 0.1083 | 0.0244 | 0.1083 |
| McNemar test-Endpoint-p-value | 0.0412 | 0.2482 | 0.0412 | 0.4795 |
| McNemar test-Directional-p-value | 0.1306 | 0.0412 | 0.1306 | 0.0736 |

|  | Species Only-Relative Proportions | | | | | | Species + Genera-Relative Proportions | | | | | |
|---|---|---|---|---|---|---|---|---|---|---|---|---|
|  | Baseline to Post6 | | | Post6 to Post18 | | | Baseline to Post6 | | | Post6 to Post18 | | |
| Plaque Only: | Baseline | Post6 | FC* | Post6 | Post18 | FC* | Baseline | Post6 | FC* | Post6 | Post18 | FC* |
| Mean: Disease (Health) | −0.0556 | 0.2598 | 5.673 | 0.2908 | 0.0764 | −0.263 | −0.0261 | 0.3207 | 13.287 | 0.3531 | 0.1630 | −0.462 |
| Std Dev | 0.1624 | 0.2928 |  | 0.1332 | 0.2021 |  | 0.1912 | 0.2746 |  | 0.0789 | 0.2142 |  |
| Median | −0.1023 | 0.2727 |  | 0.3354 | 0.0294 |  | −0.0860 | 0.3359 |  | 0.3933 | 0.1996 |  |

*FC is fold change in Average Relative Proportion (%) from Baseline to P6 and P6 to P18 per HOMINGS for "Caries-free" and "Caries-active" associated species as defined by Tanner ACR et al., 2016 ("Species Only"), or with the addition of other known species corresponding to genera of species defined by Tanner et al., 2016 ("Species + Genera"). A positive or negative value corresponds to a change toward disease or health respectively. p-values have not been corrected for false discovery.

TABLE 9

Ten Greatest Relative Proportion Changes (%) in Dental Plaque from BL to P6 for "Species Only" and "Species + Genera"*

|  | From BL to P6 Relative Proportion (%) | |
|---|---|---|
| Plaque Sample Site | Toward Disease | Toward Health |
| Species Only | | |
| *Streptococcus mutans* | 11.0 | |
| *Streptococcus sanguinis* | 4.7 | |
| *Prevotella melaninogenica* | 3.1 | |
| *Rothia dentocariosa* | 2.9 | |
| *Gemella haemolysans* | 2.4 | |
| *Actinomyces gerencseriae* | 2.2 | |
| *Scardovia wiggsiae* | 2.0 | |

TABLE 9-continued

Ten Greatest Relative Proportion Changes (%) in Dental Plaque from BL to P6 for "Species Only" and "Species + Genera"*

|  | From BL to P6 Relative Proportion (%) | |
|---|---|---|
| Plaque Sample Site | Toward Disease | Toward Health |
| *Abiotrophia defectiva* | 1.4 | |
| *Veillonella parvula* | 0.7 | |
| *Veillonella atypica* | 1.0 | |
| All Other | 1.6 | 1.4 |
|  | 33.0 | 1.4 |

TABLE 9-continued

Ten Greatest Relative Proportion Changes (%) in Dental Plaque from BL to P6 for "Species Only" and "Species + Genera"*

| Plaque Sample Site | From BL to P6 Relative Proportion (%) | |
|---|---|---|
| | Toward Disease | Toward Health |
| Species + Genera | | |
| Streptococcus mutans | 11.0 | |
| Streptococcus sanguinis | 4.7 | |
| Prevotella melaninogenica | 3.1 | |
| Rothia dentocariosa | 2.9 | |
| Gemella haemolysus | 2.4 | |
| Actinomyces gerencseriae | 2.2 | |
| Scardovia wiggsiae | 2.0 | |
| Abiotrophia defectiva | 1.4 | |
| Streptococcus anginosus | 1.3 | |
| Veillonella atypica | 1.0 | |
| All Other | 5.6 | 2.9 |
| | 37.6 | 2.9 |

*Greatest changes in relative abundance by HOMINGS for "Caries-free" and "Caries-active" associated species as defined by Tanner ACR et al., 2016 ("Species Only"), or with the addition of other known species corresponding to genera of species defined by Tanner et al., 2016 ("Species + Genera"). S. Sanguinis considered as Health-associated Species.

TABLE 10

Ten Greatest Relative Proportion Changes (%) in Dental Plaque for P6 to P18 for "Species Only" and "Species + Genera"*

| Plaque Sample Site | From P6 to P8 Relative Proportion (%) | |
|---|---|---|
| | Toward Disease | Toward Health |
| Species Only | | |
| Streptococcus mutans | | 9.1 |
| Gemella haemolysus | | 6.9 |
| Rothia dentocariosa | | 5.5 |
| Veillonella dispar | 4.7 | |
| Streptococcus intermedius | 0.2 | |
| Actinomyces gerencseriae | | 2.8 |
| Abiotrophia defectiva | | 0.2 |
| Veillonella atypica | | 0.3 |
| Streptococcus sanguinis | | 1.3 |
| Corynebacterium matruchotii | 0.3 | |
| All Other | 0.5 | 0.9 |
| | 5.4 | 26.8 |
| Species + Genera | | |
| Streptococcus mutans | | 9.1 |
| Gemella haemolysus | | 6.9 |
| Rothia dentocariosa | | 5.5 |
| Veillonella dispar | 4.7 | |
| Actinomyces sp oral taxon 448 | 2.9 | |
| Actinomyces gerencseriae | | 2.8 |
| Selenomonas noxia | 1.6 | |
| Streptococcus anginosus | | 1.6 |
| Streptococcus sanguinis | | 1.3 |
| Actionmyces massiliensis | | 0.6 |
| All Other | 2.0 | 2.4 |
| | 11.2 | 30.2 |

*Greatest changes in relative abundance by HOMINGS for "Caries-free" and "Caries-active" associated species as defined by Tanner ACR et al., 2016 ("Species Only"), or with the addition of other known species corresponding to genera of species defined by Tanner et al., 2016 ("Species + Genera"). S. Sanguinis considered as Health-associated Species.

What is claimed is:

1. A method of treating a subject having an increased risk of developing oral complications associated with radiation therapy and/or chemotherapy, comprising:
a) obtaining an oral sample from the subject;
b) contacting the oral sample from the subject with reagents for detection of the presence of and associated bacterial gene expression of each of the microbial species: Abiotrophia defectiva, Actinomyces gerencseriae, Actinomyces israelii, Actinomyces meyeri, Actinomyces naeslundii, Actinomyces odontolyticus AC-37, Actinomyces odontolyticus AC-14, Alloprevotella tannerae, Atopobium parvulum AT-08, Atopobium parvulum AT-02, Atopobium rimae, Bacteroidaceae [G1] sp oral taxon 272, Bacteroidales [G2] sp oral taxon 274, Bifidobacterium dentium, Bifidobacterium longum, Campylobacter concisus CA-02, Campylobacter concisus CA-01, Campylobacter curvus, Campylobacter gracilis, Capnocytophaga gingivalis, Capnocytophaga sputigena, Cardiobacterium hominis, Corynebacterium matruchotii, Cryptobacterium curtum, Desulfobulbus sp oral taxon 041, Dialister invisus, Dialister pneumosintes, Eikenella corrodens, Enterococcus faecalis, Eubacterium [11][G-1] infirmum, Eubacterium [11][G-3] brachy, Eubacterium [11][G-5] saphenum, Fretibacterium fastidiosum, Fretibacterium sp oral taxon 360, Fusobacterium nucleatum subsp animalis, Fusobacterium nucleatum subsp nucleatum, Fusobacterium nucleatum subsp polymorphum, Fusobacterium nucleatum subsp vincentii, Fusobacterium periodonticum, Gemella haemolysans, Gemella morbillorum GE-03, Gemella morbillorum GE-05, Granulicatella elegans, Haemophilus parainfluenzae, Lachnoanaerobaculum saburreum, Lachnospiraceae [G2] sp oral taxon 096, Lachnospiraceae [G7] sp oral taxon 086, Lactobacillus fermentum, Lactobacillus salivarius, Lactococcus lactis, Lautropia mirabilis, Leptotrichia wadei, Megasphaera micronuciformis, Mogibacterium timidum, Neisseria bacilliformis, Neisseria elongata, Neisseria flavescens, Parascardovia denticolens, Parvimonas micra, Porphyromonas endodontalis, Porphyromonas gingivalis, Prevotella denticola, Prevotella melaninogenica, Prevotella nigrescens, Prevotella oralis, Prevotella oris, Prevotella pallens, Prevotella veroralis, Pseudoramibacter alactolyticus, Rothia dentocariosa, Scardovia wiggsiae, Selenomonas noxia SE-05, Selenomonas noxia SE-04, Selenomonas sputigena SE-32, Selenomonas sputigena SE-18, Selenomonas sputigena SE-19, Shuttleworthia satelles, Solobacterium moorei, Streptococcus anginosus, Streptococcus constellatus, Streptococcus intermedius, Streptococcus mutans, Streptococcus parasanguinis II, Streptococcus sanguinis, Tannerella forsythia, Veillonella atypica VE-20, Veillonella atypica VE-21, Veillonella denticariosi, Veillonella dispar, Veillonella parvula VE-06, Veillonella parvula VE-05, and Veillonellaceae [G1] sp oral taxon 155;
c) detecting the presence and associated bacterial gene expression of one or more of the microbial species of step (b);
d) determining an oral microbiome signature of the subject based on the microbial species detected and the associated gene expression of the microbial species detected in step (c);
e) comparing the oral microbiome signature of the subject as determined in step (d) with an oral microbiome biomarker profile determined to be correlated with oral complications associated with radiation therapy and/or chemotherapy, wherein an oral microbiome signature of the subject having one or more biomarkers of the oral microbiome biomarker profile identifies the subject as having an increased risk of developing oral complications associated with radiation therapy and/or chemotherapy; and f) treating the subject having an increased risk of developing oral complications associated with radiation therapy and/or chemotherapy, wherein the oral complication is caries and the treatment is fluoride, fillings, crowns, root canals, and/or extraction;

wherein the oral complication is periodontitis and the treatment is professionally cleaning pockets around teeth to prevent damage to surrounding bone and/or surgery;

wherein the oral complication is xerostomia and the treatment is administering an oral rinse to restore mouth moisture, administering salagen, chewing sugar-free gum, limiting caffeine intake, stopping tobacco use, drinking water, using an over-the-counter saliva substitute, and/or sleeping with a humidifier; and/or wherein the oral complication is oral mucositis and the treatment is improving oral hygiene, administering painkillers in a mouth rinse, gel, or spray, and/or taking palifermin.

2. The method of claim 1, wherein the oral sample is obtained from the subject prior to administration of radiation therapy and/or chemotherapy to the subject.

3. The method of claim 1, wherein the oral sample is obtained from the subject while the subject is undergoing a radiation therapy and/or chemotherapy treatment regimen and/or after administration of radiation therapy and/or chemotherapy to the subject.

4. The method of claim 1, wherein step (c) is carried out with Next Generation Sequencing (NGS) technology and quantitative reverse transcriptase polymerase chain reaction (qRT-PCR) technology.

* * * * *